United States Patent
Bartkovitz et al.

(10) Patent No.: US 8,993,614 B2
(45) Date of Patent: Mar. 31, 2015

(54) SUBSTITUTED PYRROLIDINE-2-CARBOXAMIDES

(71) Applicant: Hoffmann-La Roche Inc., Newark, NJ (US)

(72) Inventors: David Joseph Bartkovitz, Nutley, NJ (US); Xin-Jie Chu, Shanghai (CN); Binh Thanh Vu, North Caldwell, NJ (US); Chunlin Zhao, Shanghai (CN); Daniel Fishlock, Basel (CH)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/785,267

(22) Filed: Mar. 5, 2013

(65) Prior Publication Data

US 2013/0244958 A1 Sep. 19, 2013

Related U.S. Application Data

(60) Provisional application No. 61/611,200, filed on Mar. 15, 2012.

(51) Int. Cl.
| | | |
|---|---|---|
| *A01N 43/38* | (2006.01) | |
| *A61K 31/40* | (2006.01) | |
| *C07D 403/12* | (2006.01) | |
| *C07D 207/16* | (2006.01) | |
| *C07F 9/572* | (2006.01) | |
| *C07H 15/26* | (2006.01) | |
| *C07D 405/12* | (2006.01) | |
| *C07D 493/04* | (2006.01) | |

(52) U.S. Cl.
CPC ............ *C07D 403/12* (2013.01); *C07D 207/16* (2013.01); *C07F 9/572* (2013.01); *C07H 15/26* (2013.01); *C07D 405/12* (2013.01); *C07D 493/04* (2013.01); *C07F 9/5727* (2013.01)
USPC ........... 514/411; 514/359; 514/381; 514/408; 514/410

(58) Field of Classification Search
None
See application file for complete search history.

(56) References Cited

U.S. PATENT DOCUMENTS

| | | | |
|---|---|---|---|
| 5,906,977 | A | 5/1999 | Sinn et al. |
| 6,165,509 | A | 12/2000 | Hoffman et al. |
| 6,713,454 | B1 | 3/2004 | Ekwuribe et al. |
| 7,759,383 | B2 | 7/2010 | Wang et al. |
| 2002/0110535 | A1 | 8/2002 | Jones |
| 2003/0162953 | A1 | 8/2003 | Coutts et al. |
| 2005/0004031 | A1 | 1/2005 | Subasinghe et al. |
| 2005/0033058 | A1 | 2/2005 | Huang et al. |
| 2005/0107277 | A1 | 5/2005 | Lin et al. |
| 2006/0046967 | A1 | 3/2006 | Satyam |
| 2010/0048483 | A1 | 2/2010 | Yang et al. |
| 2013/0052130 | A1 | 2/2013 | Davis et al. |

FOREIGN PATENT DOCUMENTS

| | | |
|---|---|---|
| CN | 101991860 | 3/2011 |
| CN | 102247602 | 11/2011 |
| EP | 0354855 | 2/1990 |
| EP | 0452179 | 10/1991 |
| EP | 1405871 | 4/2004 |
| JP | 2008308690 | 12/2008 |
| WO | 9506058 | 3/1995 |
| WO | 9516465 | 6/1995 |
| WO | 9704796 | 2/1997 |
| WO | 9832466 | 7/1998 |
| WO | 9917120 | 4/1999 |
| WO | 0050007 | 8/2000 |
| WO | 2005094897 | 10/2005 |
| WO | 2006047419 | 5/2006 |
| WO | 2007127473 | 11/2007 |
| WO | 2008109783 | 9/2008 |
| WO | 2009128789 | 10/2009 |
| WO | 2009155431 | 12/2009 |
| WO | 2010007626 | 1/2010 |
| WO | 2010151269 | 12/2010 |
| WO | 2011061139 | 5/2011 |
| WO | 2011/098398 | 8/2011 |
| WO | 2012034954 | 3/2012 |
| WO | 2012065022 | 5/2012 |
| WO | 2012103634 | 8/2012 |
| WO | 2012116073 | 8/2012 |

OTHER PUBLICATIONS

Pendri et al., "PEG Modified Anticancer Drugs: Synthesis and Biological Activity" Journal of Bioactive and Compatible Polymers 11(2):122-134 (Apr. 1996).
Pendri et al., "Poly(ethylene glycol) fluorescent linkers" Bioconjug Chem 6(5):596-8. (Sep. 1995).
Conover et al., "Camptothecin delivery systems: enhanced efficacy and tumor accumulation of camptothecin following its conjugation to polyethylene glycol via a glycine linker" Cancer Chemotherapy and Pharmacolgy 42(5):407-414 (Sep. 1998).
Greenwald et al., "Drug delivery of anticancer agents: water soluble 4-poly (ethylene glycol) derivatives of the lignan, podophyllotoxin," J Control Release. 61(3):281-94 (Sep. 20, 1999).

(Continued)

*Primary Examiner* — Patrick Lewis

(57) ABSTRACT

There are provided compounds of the formula

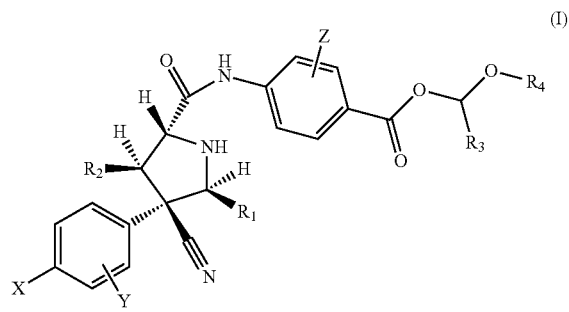

(I)

wherein X, Y, Z, $R_1$, $R_2$, $R_3$ and $R_4$ are as described herein and enantiomers and pharmaceutically acceptable salts and esters thereof. The compounds are useful as anticancer agents.

27 Claims, No Drawings

(56) References Cited

OTHER PUBLICATIONS

Liu et al., "Amphipathic polyethylene glycol stabilized emulsions (o/w): Physical characterization and in vivo distribution," International Journal of Pharmaceutics 125(1):73-80 (Oct. 17, 1995).

Zalipsky, "Functionalized Poly(ethylene glycol) for Preparation of Biologically Relevant Conjugates" Bioconjugafe Chem(6):150-1 65 (1995).

Greenwald et al., "Drug delivery systems employing 1,4- or 1,6-elimination: poly(ethylene glycol) prodrugs of amine-containing compounds," J Med. Chem. Sep. 9, 1999;42(18):3657-67.

Greenwald et al., "Drug Delivery Systems: Water Soluble Taxol 2¢-Poly(ethylene glycol) Ester ProdruggsDesign and in Vivo Effectiveness," J. Med. Chem. 39:424-431 (1996).

Nudelman et al., "Prodrugs of butyric acid. Novel derivatives possessing increased aqueous solubility and potential for treating cancer and blood diseases," Eur. J. Med. Chem. 36 (2001) 63-74., pp. 12.

The International Search Report and Written Opinion, issued on May 24, 2013, in the corresponding PCT Patent Application No. PCT/EP2013/054920., pp. 13.

The letter of opposition in the corresponding Costa Rican Application No. 2014-0399, notified by the Costa Rican Patent Office on Jan. 12, 2015.

SUBSTITUTED PYRROLIDINE-2-CARBOXAMIDES

PRIORITY TO RELATED APPLICATION(S)

This application claims the benefit of U.S. Provisional Application No. 61/611,200, filed Mar. 15, 2012, which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to pyrrolidine-2-carboxamide derivatives I which act as antagonists of mdm2 interactions and hence are useful as potent and selective anticancer agents. The present compounds are of the general formula

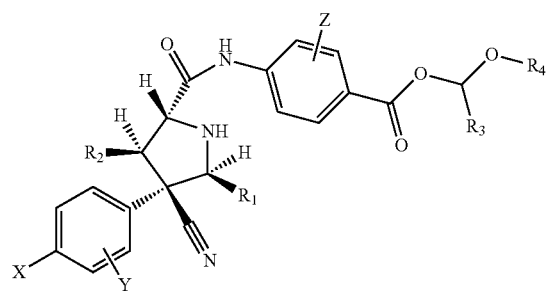

wherein X, Y, Z, $R_1$, $R_2$, $R_3$ and $R_4$ are as described herein and enantiomers and pharmaceutically acceptable salts and esters thereof.

DETAILED DESCRIPTION OF THE INVENTION

There are provided compounds of the formula

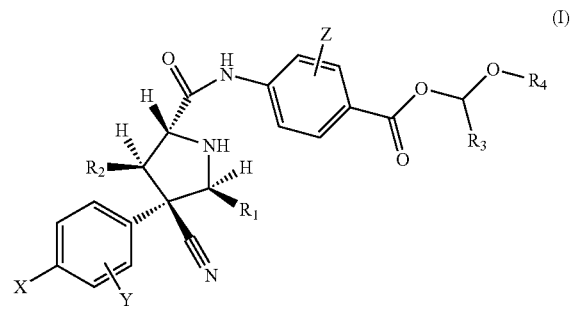

wherein
X is selected from the group consisting of H, F, Cl, Br, I, cyano, nitro, ethynyl, cyclopropyl, methyl, ethyl, isopropyl, vinyl and methoxy,
Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl,
Z is lower alkoxy,
$R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl,
$R_2$ is a substituted phenyl selected from:

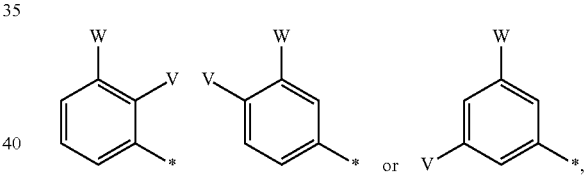

W is F, Cl or Br,
V is H or F,
$R_3$ is selected from the group consisting of hydrogen, lower alkyl or substituted lower alkyl,
$R_4$ is selected from the group consisting of:

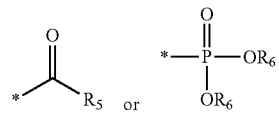

$R_5$ is selected from the group consisting of lower alkyl, substituted lower alkyl, heterocycle, substituted heterocycle, cycloalkyl, substituted cycloalkyl, natural and unnatural amino acids, —(OCH$_2$CH$_2$)$_n$—OH, —(OCH$_2$CH$_2$)$_n$—OCH$_3$, —(NCH$_2$CH$_2$)$_n$—OH, —(NCH$_2$CH$_2$)$_n$—OCH$_3$ and —(OCH$_2$CH$_2$)$_n$—OP(O)(OR$_6$)$_2$, wherein n is from 3 to 60,
$R_6$ is hydrogen or benzyl
or a pharmaceutically acceptable salt or ester thereof.
Alternatively there are compounds wherein
X is selected from H, F or Cl,
Y is selected from H, F or Cl,
$R_1$ is lower alkyl or substituted lower alkyl, R₃ is hydrogen or lower alkyl,
R₅ is selected from the group consisting of lower alkyl, substituted lower alkyl, natural and unnatural amino acids, —(OCH₂CH₂)ₙ—OH, —(OCH₂CH₂)ₙ—OCH₃, —(NCH₂CH₂)ₙ—OH, —(NCH₂CH₂)ₙ—OCH₃, —(OCH₂CH₂)ₙ—OP(O)(OR₆)₂, wherein n is from 40-60 and
R₆ is hydrogen
or a pharmaceutically acceptable salt thereof.
Alternatively there are compounds wherein
X is selected from H, F or Cl,
Y is selected from H, F or Cl,
R₁ is lower alkyl or substituted lower alkyl,
R₃ is hydrogen or lower alkyl,
R₅ is selected from —(OCH₂CH₂)ₙ—OH or —(OCH₂CH₂)ₙ—OCH₃ wherein n is from 45-55 and
R₆ is hydrogen
or a pharmaceutically acceptable salt thereof.
Alternatively there are compounds where
R₅ is selected from —(OCH₂CH₂)ₙ—OH or —(OCH₂CH₂)ₙ—OCH₃ wherein n is about 45-50.
Alternatively there are compounds selected from 1-(Ethyl(isopropyl)carbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid di-tert-butoxy-phosphoryloxymethyl ester,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[bis-(2-methoxy-ethyl)-carbamoyloxy]-ethyl ester,
4-Methyl-piperazine-1-carboxylic acid 1-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethyl ester,
1-Acetoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
Rac-1-(isobutyryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid acetoxymethyl ester,
1-(Cyclohexyloxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
Rac-1-(isopropoxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethyl morpholine-4-carboxylate,
Morpholine-4-carboxylic acid (R)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester,
Morpholine-4-carboxylic acid (S)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester,
Rac-1-tert-butyl 4-(1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl)piperazine-1,4-dicarboxylate,
piperazine-1-carboxylic acid 1-(4-{[(2R,3S,4R,5S)-4-(4-chloro-2-fluoro-phenyl)-3-(3-chloro2-fluoro-phenyl)-4-cyano-5-(2,2-dimethyl-propyl)-pyrrolidine-2-carbonyl]-amino}-3-methoxy-benzoyloxy)-ethyl ester di-hydrochloride,
Rac-1,1-Dioxo-thiomorpholine-4-carboxylic acid 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester,
4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,2-dimethyl-[1,3]dioxolan-4-ylmethylcarbamoyloxy)-ethyl ester,
4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,3-dihydroxy-propylcarbamoyloxy)-ethyl ester,
1-(Tetrahydro-2H-pyran-4-ylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-{2-[2-(2-methoxy-ethoxy)-ethoxy]-ethoxycarbonyloxy}-ethyl ester,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-methoxy-ethoxy)-ethoxy]-ethoxy}-ethoxycarbonyloxy)-ethyl ester,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[2-(2-{2-[2-(2-methoxy-ethoxy)-ethoxy]-ethoxy}-ethoxy)-ethoxycarbonyloxy]-ethyl ester,
21-oxo-2,5,8,11,14,17,20,22-octaoxatetracosan-23-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000) (Average MW: ~2695),
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2300) (Average MW: ~2900),
1-(2-(Benzyloxy)-2-oxoethylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
2-((1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethoxy)carbonylamino)acetic acid, (S)-2-[1-(4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethoxycarbonylamino]-pentanedioic acid, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-((S)-1-carboxy-ethylcarbamoyloxy)-ethyl ester, 2-(((4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)methoxy)-carbonylamino)acetic acid, (S)-Dibenzyl 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)pentanedioate, (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)pentanedioic acid, 15-methyl-12-oxo-2,5,8,11,13-pentaoxahexadecan-14-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 3-Oxo-2,4,7,10,13,16,19-heptaoxaicosyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester, 3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 27-Oxo-2,5,8,11,14,17,20,23,26,28-decaoxatriacontan-29-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 24-Oxo-2,5,8,11,14,17,20,23,25-nonaoxaheptacosan-26-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)propanoic acid, Dibenzyl 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid phosphonooxymethyl ester; compound with trifluoroacetic acid, 1-(((3aR,5R,6S,6aR)-5-((R)-2,2-dimethyl-1,3-dioxolan-4-yl)-2,2-dimethyltetrahydrofuro[3,2-d][1,3]dioxol-6-yloxy)carbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[(2R,3R,4R,5S)-2-((R)-1,2-dihydroxy-ethyl)-4,5-dihydroxy-tetrahydro-furan-3-yloxycarbonyloxy]-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-dibenzyloxyphosphoryloxy-ethoxy)-ethoxy]-ethoxy}-ethoxycarbonyloxy)-ethyl ester and 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-phosphonooxy-ethoxy)-ethoxy]-ethoxy}-ethoxycarbonyloxy)-ethyl ester.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-2-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkyl-sulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carboxy lower alkoxy, oxo and CN. Preferred substituents for alkyl are alkoxy and N(lower alkyl)$_2$.

The term "mPEG" as used herein means methoxy polyethylene glycol, which is commercially available (e.g. Sigma-Aldrich or ID Biochem (Korea)). The molecular weight distribution of mPEG may vary according to the manufacturer and/or batch. In one embodiment of the present invention, mPEG has an average molecular weight (MW) of about 1500 Da to about 3000 Da. In another embodiment of the present invention mPEG has an average MW of about 2000 Da and about 2300 Da. Average MW is determined by MALDI-TOF mass spectrometry.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl. Where the aryl group is bicyclic a preferred group is 1,3-dioxo-2,3-dihydro-1H-isoindol-5-yl group.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted. "Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxyphosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors. The compounds may also be useful in the treatment of certain non-solid tumors such as leukemia's and lymphoma's.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

In solution the compounds of the present invention can form micellular structures having a particle size of between 10 to 100 nanometers.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit MDM2 interaction with p53. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention are especially useful when dosed parenterally or infusionally due to their superior solubility and longer plasma half life when compared to their non-esterified/non-amide parent compound. Further the compounds of the present invention exhibit superior PK nonvariability when compared to their parent compounds. With regard to solubility, the compound of Example 37 (Compound A)

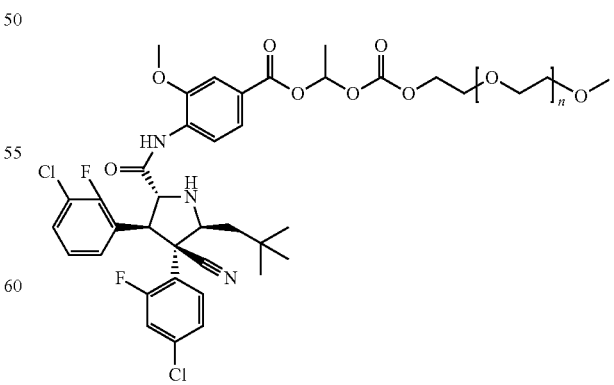

exhibits an aqueous solubility in excess of 30 mg/ml whereas it's parent compound (Compound B) having the formula

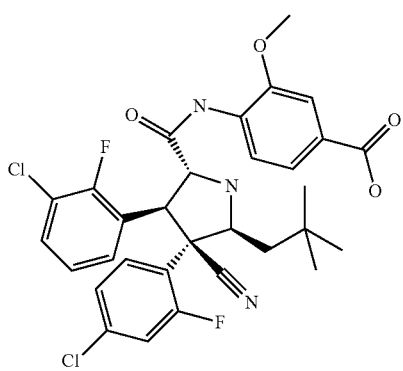 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

has an aqueous solubility of less than 1 µg/ml.

Compound A was administered intravenously (iv bolus) at a dose level of 1 mg/kg active drug equivalents (4.37 mg/kg prodrug). Compound A and Compound B were quantified in plasma by selective LC-MS/MS methods with lower limits of quantification of 1 ng/mL and 5 ng/mL, respectively.

The main results (Mean, N=2) were the following:

PK data for Compound A (prodrug): 4.37 mg/kg iv (corresponding to 1 mg/kg active parent compound) (N=2): Cmax=142000 ng/mL, apparent terminal half-life t½=2.59 h, AUC(0–inf)=108000 (ng·h)/mL, AUC(0–tlast) =108000 (ng·h)/mL, CL=0.709 mL/min·kg and Vss=0.0235 L/kg.

PK data for Compound B (active drug): 4.37 mg/kg Compound A iv (corresponding to 1 mg/kg active parent compound) (N=2): Cmax=4390 ng/mL, apparent terminal half-life t½=5.07 h, AUC(0–inf)=21600 (ng·h)/mL and AUC (0–tlast)=20900 (ng·h)/mL.

In conclusion, the prodrug showed very low plasma clearance and volume of distribution, associated with a moderate half-life. Significant conversion to active drug was achieved. Furthermore, only very little prodrug or active drug were recovered into urine.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The general method for the preparation of compounds of formula I is given in Scheme 1. Briefly, the process involves alkylation of the benzoic acid (II) with the chloro compound (III) in the presence of a base such as cesium carbonate. Compounds of Formula II are known in the art, see, for example, US 2010/0152190-A1. The chloro compound (III) is typically prepared by reaction of 1-chloroalkyl chloroformate with alcohol or amine in the presence of a base such as pyridine.

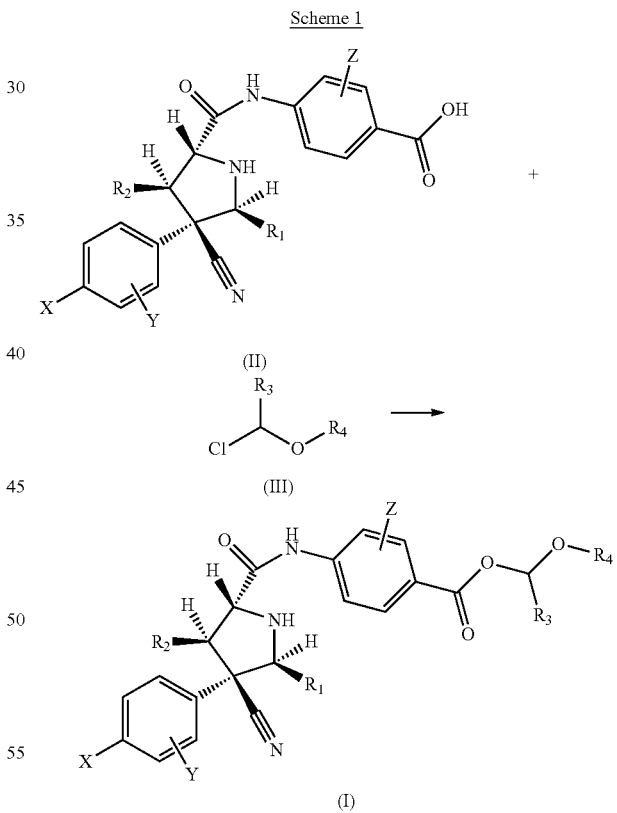

The compounds of the invention can be prepared by processes known in the art. Suitable processes for synthesizing these compounds are provided in the examples. Average MW's in the examples were obtained with MALDI-TOF mass spectrometry.

The following examples and references are provided to aid the understanding of the present invention. However, the true scope of the invention is set forth in the appended claims.

EXAMPLE 1

1-(Ethyl(isopropyl)carbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

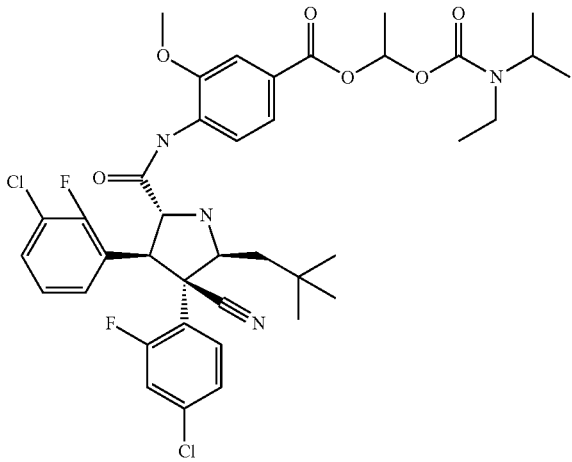

M.W. 773.71,
$C_{39}H_{44}Cl_2F_2N_4O_6$

EXAMPLE 2

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid di-tert-butoxy-phosphoryloxymethyl ester

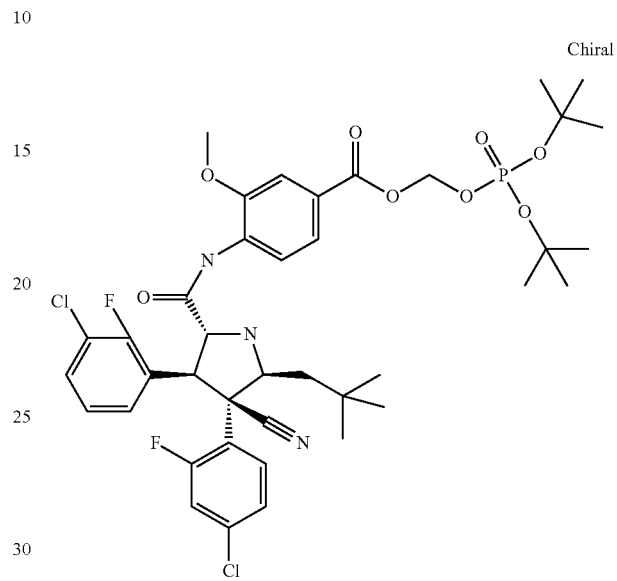

M.W. 838.72, $C_{40}H_{48}Cl_2F_2N_3O_8P$

To a cooled solution of 2-propanol (1.57 g, 2 mL, 26.1 mmol) and N,N-diisopropylethylamine (6.75 g, 9.13 mL, 52.3 mmol) in methylene chloride (15 mL) was added 1-chloroethyl carbonochloridate (Aldrich, 4.11 g, 28.7 mmol) slowly at 0° C. After addition the reaction mixture was allowed to stir at room temperature overnight. The mixture was concentrated to dryness and the crude material which contained approximately 50% of ethyl-isopropyl-carbamic acid 1-chloro-ethyl ester was used for the next step without further purification.

To a solution of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 150 mg, 0.243 mmol) in dimethylformamide (6 mL) was added cesium carbonate (243 mg, 0.746 mmol). After stirring for a few minutes, a solution of the above freshly made ethyl-isopropyl-carbamic acid 1-chloro-ethyl ester (190 mg, 0.491 mmol) in dry dimethylformamide (1 mL) was added and the reaction mixture was allowed to stir at room temperature overnight. This reaction mixture was diluted with ethyl acetate and washed with water, brine and concentrated to dryness. The crude material was purified by chromatography (hexane/ethyl acetate, 90/10 to 10/90) to give 1-(ethyl(isopropyl)-carbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid (102 mg, 54% yield). LCMS (ES$^+$) m/z calcd. for $C_{39}H_{45}Cl_2F_2N_4O_6$ [(M+H)$^-$]: 773, found: 773.

To a solution of potassium di-tert-butylphosphate (2.45 g, 9.51 mmol), sodium bicarbonate (3.19 g, 38.0 mmol) and tetrabutylammonium hydrogen sulfate (340.2 mg, 0.972 mmol) in water (80 mL), was added methylene chloride (50 mL). The mixture was cooled to 0° C. and stirred vigorously under argon for 10 min. Chloromethyl chlorosulfate (1.92 g, 1.2 mL, 11.6 mmol) in methylene chloride (30 mL) was added slowly and the reaction was stirred at room temperature overnight. The organic layer was separated, washed with brine and dried over anhydrous sodium sulfate and concentrated to give di-tert-butyl chloromethyl phosphate as a colorless oil (1.46 g, 59% yield).

To a solution of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 200.0 mg, 0.324 mmol) in dimethylformamide (8 mL) was added cesium carbonate (529 mg, 1.62 mmol). The mixture was stirred for ~20 min before di-tert-butyl chloromethyl phosphate (TCI, 236 mg, 0.9912 mmol) in dimethylformamide (1 mL) was added. The reaction mixture was allowed to stirr at room temperature for 3 h before it was partitioned between ethyl acetate and water, washed with water and dried over anhydrous sodium sulfate and concentrated. The crude product was purified by flash chromatography (hexane/ethyl acetate, 85/15 to 5/95) to give chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid di-tert-butoxy-phosphoryloxymethyl ester as a white solid (192 mg, 70% yield). LCMS (ES$^+$) m/z calcd. for $C_{40}H_{49}Cl_2F_2N_3O_8P$ [(M+H)$^+$]: 838, found: 838.

EXAMPLE 3

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[bis-(2-methoxy-ethyl)-carbamoyloxy]-ethyl ester

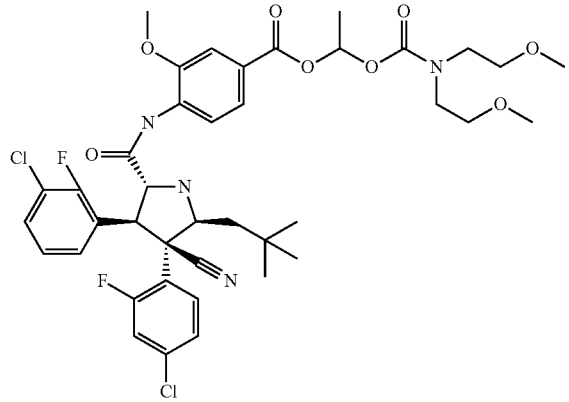

MW 819.74
$C_{40}H_{46}Cl_2F_2N_4O_8$

To a cooled solution of bis(2-methoxyethyl)amine (1.94 g, 14.5 mmol, Aldrich) and pyridine (1.26 g, 1.29 mL, 15.9 mmol) in methylene chloride (18 mL) at −78° C., was added slowly 1-chloroethyl carbonochloridate (1.98 g, 1.5 mL, 13.8 mmol, Aldrich) over ~15 min. The reaction mixture was allowed to stir at −78° C. for 3 h, giving a white precipitate. This cold reaction mixture was filtered to remove the solid and the filtrate was concentrated to dryness, giving the crude 1-chloroethyl bis(2-methoxyethyl)carbamate used for the next step without further purification.

To a solution of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (US20100152190A1, 200 mg, 0.324 mmol) in dimethylformamide (8 mL) was added cesium carbonate (846 mg, 2.6 mmol). After stirring for 10 min, a solution of the above freshly made 1-chloroethyl bis(2-methoxyethyl)carbamate (510 mg, 2.13 mmol) in dimethylformamide (3 mL) was added. The reaction mixture was allowed to stir at room temperature overnight. This reaction mixture was taken up in ethyl acetate, washed with water, brine and concentrated to dryness. The crude material was purified by flash chromatography (hexane/ethyl acetate, 90/10 to 10/90) to give 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[bis-(2-methoxy-ethyl)-carbamoyloxy]-ethyl ester as a white solid (168 mg, 63% yield). LCMS (ES⁺) m/z calcd. for $C_{40}H_{47}Cl_2F_2N_4O_8$ [(M+H)⁺]: 819, found: 819.

EXAMPLE 4

4-Methyl-piperazine-1-carboxylic acid 1-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethyl ester

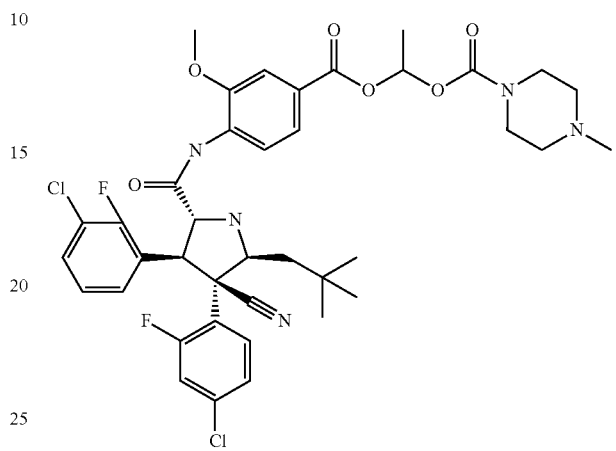

M.W. 786.71,
$C_{39}H_{43}Cl_2F_2N_5O_6$

In a manner similar to the method described in Example 3, 1-chloroethyl carbonochloridate was reacted with 1-methylpiperazine and pyridine in methylene chloride at −78° C. for 3 h to give 1-chloroethyl 4-methylpiperazine-1-carboxylate hydrochloride salt which was reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 4-methyl-piperazine-1-carboxylic acid 1-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethyl ester as a white solid. LCMS (ES⁺) m/z calcd. for $C_{39}H_{44}Cl_2F_2N_5O_6$ [(M+H)⁺]: 786, found: 786.

EXAMPLE 5

Acetoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

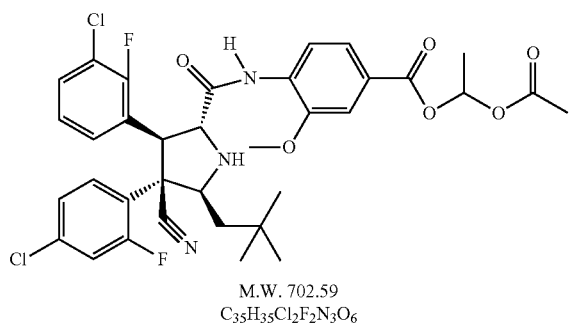 [SMILES: COc1cc(C(=O)OC(C)OC(C)=O)ccc1NC(=O)[C@@H]1N[C@@H](CC(C)(C)C)[C@](C#N)(c2ccc(Cl)cc2F)[C@H]1c1cccc(Cl)c1F]

M.W. 702.59
$C_{35}H_{35}Cl_2F_2N_3O_6$

A mixture of paraldehyde (JT-Baker, 1.39 g, 1.4 mL, 10.5 mmol) and sodium iodide (5.01 g, 33.4 mmol) in methylene chloride (75 mL) were treated with acetyl chloride (2.21 g, 2 mL, 27.8 mmol) in methylene chloride (25 mL) over 20 min and allowed to stir at room temperature in the dark for 18 h. The reaction mixture was filtered and concentrated to give 1-iodoethyl acetate as a brown oil.

To a mixture of the above 1-iodoethyl acetate (311 mg, 1.457 mmol) and chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (US20100152190A1, 201.7 mg, 0.327 mmol) in dimethylformamide (6 mL) was added cesium carbonate (659 mg, 2.00 mmol) and the mixture was stirred at room temperature for 16 h. The reaction mixture was taken up in ethyl acetate, washed with water and then brine. The organic layer was dried over sodium sulfate and concentrated to dryness. The crude material was purified by flash chromatography (hexane/ethyl acetate, 80/20 to 20/80) to give 1-acetoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (149.4 mg, 65% yield). MS (ES$^+$) m/z calcd. for $C_{35}H_{36}Cl_2F_2N_3O_6$: [(M+H)$^+$]: 702.19, found: 702.4

EXAMPLE 6

Rac-1-(isobutyryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

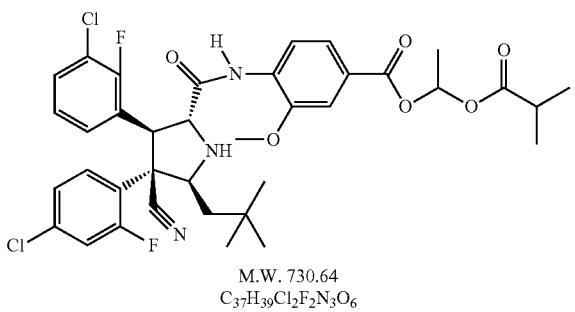 [SMILES: COc1cc(C(=O)OC(C)OC(=O)C(C)C)ccc1NC(=O)[C@@H]1N[C@@H](CC(C)(C)C)[C@](C#N)(c2ccc(Cl)cc2F)[C@H]1c1cccc(Cl)c1F]

M.W. 730.64
$C_{37}H_{39}Cl_2F_2N_3O_6$

In a manner similar to the method described in Example 5, paraldehyde (JT-Baker, 1.37 g, 10.4 mmol) was reacted with isobutyryl chloride (Aldrich, 2.93 g, 27.5 mmol) and sodium iodide (4.9472 g, 33.0 mmol) in methylene chloride (100 mL) at room temperature for 16 h to give 1-iodoethyl isobutyrate. A portion of this material (400.2 mg, 1.65 mmol) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (200.8 mg, 0.332 mmol) and cesium carbonate (653.2 mg, 2.00 mmol) in dimethylformamide (6 mL) at room temperature for 3 h to give 1-(isobutyryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as an off-white solid (198.8 mg, 83% yield). MS (ES$^+$) m/z calcd. for $C_{37}H_{40}Cl_2F_2N_3O_6$: [(M+H)$^+$]: 730, found: 730

EXAMPLE 7

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid acetoxymethyl ester

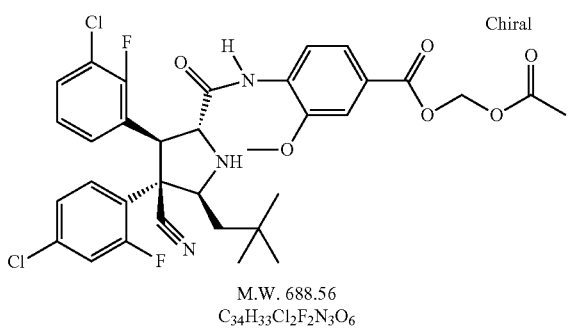 [SMILES: COc1cc(C(=O)OCOC(C)=O)ccc1NC(=O)[C@@H]1N[C@@H](CC(C)(C)C)[C@](C#N)(c2ccc(Cl)cc2F)[C@H]1c1cccc(Cl)c1F]

M.W. 688.56
$C_{34}H_{33}Cl_2F_2N_3O_6$

A mixture of 1,3,5-trioxane (Aldrich, 970.8 mg, 10.8 mmol) and sodium iodide (5.12 g, 34.2 mmol) in methylene chloride (100 mL) was treated with acetyl chloride (2.26 g, 2.1 mL, 28.5 mmol) and stirred at room temperature in the dark for 16 h. The reaction mixture was filtered and concentrated to give crude iodomethyl acetate as a brown oil.

A portion of this iodomethyl acetate (661 mg, 3.31 mmol) was added to a suspension of chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (200.1 mg, 0.325 mmol) and cesium carbonate (964.4 mg, 2.93 mmol) in dimethylformamide (8 mL) and the reaction was stirred in the dark overnight. It was then taken up in ethyl acetate, washed with water and brine, dried over anhydrous sodium sulfate and concentrated. The crude product was purified by flash chromatography (hexane/ethyl acetate, 80/20 to 10/90) to give chiral-4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid acetoxymethyl ester as a white solid (42.8 mg, 19% yield). MS (ES$^+$) m/z calcd. for $C_{34}H_{34}Cl_2F_2N_3O_6$: [(M+H)$^+$]: 688, found: 688

EXAMPLE 8

1-(Cyclohexyloxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

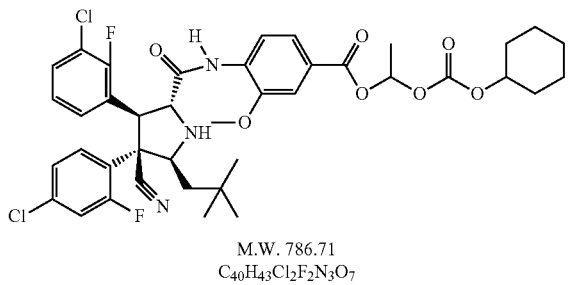 [SMILES: COc1cc(C(=O)OC(C)OC(=O)OC2CCCCC2)ccc1NC(=O)[C@@H]1N[C@@H](CC(C)(C)C)[C@](C#N)(c2ccc(Cl)cc2F)[C@H]1c1cccc(Cl)c1F]

M.W. 786.71
$C_{40}H_{43}Cl_2F_2N_3O_7$

In a manner similar to the method described in Example 3, 1-chloroethyl chloroformate (Oakwood Products, 1.99 g, 1.5 mL, 13.9 mmol) was reacted with cyclohexanol (Alfa Aesar, 1.33 g, 1.4 mL, 13.3 mmol) and pyridine (1.27 g, 1.3 mL, 16.1 mmol) in methylene chloride (11 mL) at −78° C. for 3 h to give 1-chloroethyl cyclohexyl carbonate. A portion of 1-chloroethyl cyclohexyl carbonate (253 mg, 1.22 mmol) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (150.3 mg, 0.244 mmol) in the presence of cesium carbonate (487.4 mg, 1.5 mmol) in dimethylformamide (5 mL) overnight to give, after flash chromatography purification (hexane/ethyl acetate, 80/20 to 20/80), 1-(cyclohexyloxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (135.4 mg, 70% yield). MS (ES$^+$) m/z calcd. for $C_{40}H_{44}Cl_2F_2N_3O_7$: [(M+H)$^+$]: 786, found: 786

EXAMPLE 9

Rac-1-(isopropoxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

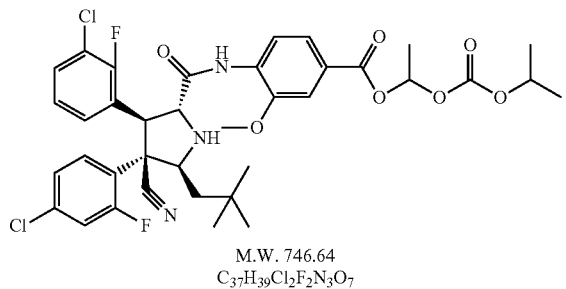 [SMILES: COc1cc(C(=O)OC(C)OC(=O)OC(C)C)ccc1NC(=O)[C@@H]1N[C@@H](CC(C)(C)C)[C@](C#N)(c2ccc(Cl)cc2F)[C@H]1c1cccc(Cl)c1F]

M.W. 746.64
$C_{37}H_{39}Cl_2F_2N_3O_7$

In a manner similar to the method described in Example 3, 1-chloroethyl chloroformate (Oakwood Products, 1.99 g, 1.5 mL, 13.9 mmol) was reacted with 2-propanol (785 mg, 1 mL, 13.0 mmol) and pyridine (1.27 g, 1.3 mL, 16.1 mmol) in methylene chloride (11 mL) at room temperature for 4 h to give 1-chloroethyl isopropyl carbonate. A portion of 1-chloroethyl isopropyl carbonate (221.6 mg, 1.33 mmol) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (150.3 mg, 244 μmol) in the presence of cesium carbonate (478 mg, 1.47 mmol) in dimethylformamide (5 mL) overnight to give, after flash chromatography purification (hexane/ethyl acetate, 80/20 to 20/80), 1-(isopropoxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (134.4 mg, 73% yield). MS (ES$^+$) m/z calcd. for $C_{37}H_{40}Cl_2F_2N_3O_7$: [(M+H)$^+$]: 746, found: 746

EXAMPLE 10

1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy) ethyl morpholine-4-carboxylate

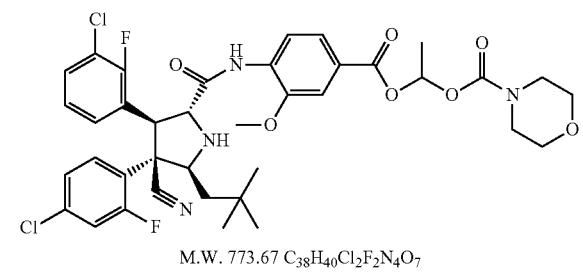 [SMILES: COc1cc(C(=O)OC(C)OC(=O)N2CCOCC2)ccc1NC(=O)[C@@H]1N[C@@H](CC(C)(C)C)[C@](C#N)(c2ccc(Cl)cc2F)[C@H]1c1cccc(Cl)c1F]

M.W. 773.67 $C_{38}H_{40}Cl_2F_2N_4O_7$

In a manner similar to the method described in Example 3, 1-chloroethyl chloroformate (2.64 g, 2 mL, 18.5 mmol) was reacted with morpholine (1.69 g, 1.7 mL, 19.4 mmol) and pyridine (1.68 g, 1.72 mL, 21.2 mmol) in methylene chloride (25 mL) at room temperature overnight to give the crude product, 1-chloroethyl morpholine-4-carboxylate. A portion of 1-chloroethyl morpholine-4-carboxylate (670.1 mg, 3.46 mmol) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (200.5 mg, 0.325 mmol) in the presence of cesium carbonate (1.094 g, 3.36 mmol) in dimethylformamide (7 mL) overnight to give, 1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl morpholine-4-carboxylate as an off-white solid (186.5 mg, 74% yield). MS (ES$^+$) m/z calcd. for $C_{38}H_{41}Cl_2F_2N_4O_7$: [(M+H)$^+$]: 773, found: 773

EXAMPLE 11

Morpholine-4-carboxylic acid (R)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester (A) and morpholine-4-carboxylic acid (S)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester (B)

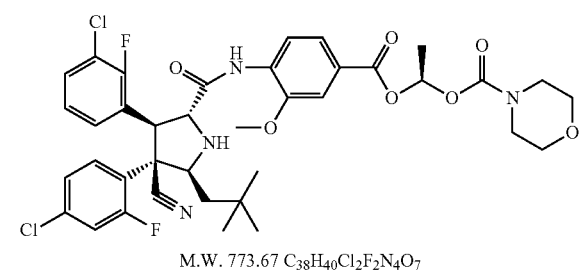

M.W. 773.67 $C_{38}H_{40}Cl_2F_2N_4O_7$

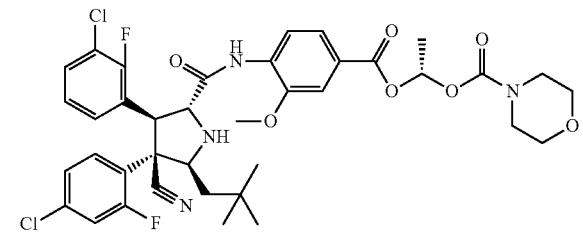

The title compounds were prepared from supercritical fluid chromatography separation of a mixture of diastereomers of 1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl morpholine-4-carboxylate (Example 10). MS (ES+) m/z calcd. for $C_{38}H_{41}Cl_2F_2N_4O_7$: [(M+H)+]: 773, found: 773

EXAMPLE 12

Rac-1-tert-butyl 4-(1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl)piperazine-1,4-dicarboxylate

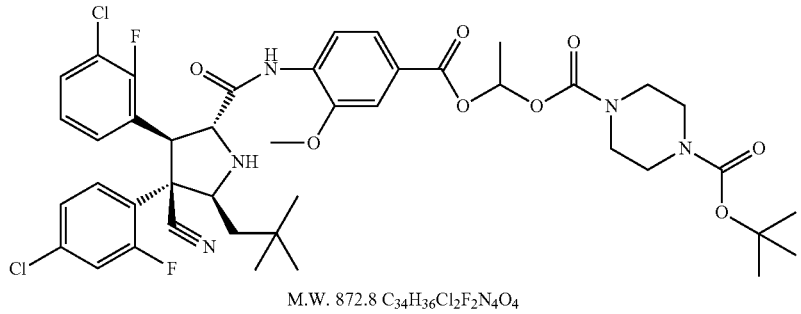 [SMILES: COc1cc(C(=O)OC(C)OC(=O)N2CCN(C(=O)OC(C)(C)C)CC2)ccc1NC(=O)[C@@H]1N[C@@H](CC(C)(C)C)[C@](C#N)(c2ccc(Cl)cc2F)[C@H]1c1cccc(Cl)c1F]

M.W. 872.8 $C_{34}H_{36}Cl_2F_2N_4O_4$

In a manner similar to the method described in Example 3, 1-chloroethyl chloroformate (Oakwood, 1.46 g, 1.1 mL, 10.2 mmol) was reacted with 1-Boc-piperazine (Alfa Aesar, 1.5756 g, 8.37 mmol) and pyridine (870 mg, 0.89 mL, 11.0 mmol) in methylene chloride (10 mL) from −78° C. for 1 h and then at room temperature overnight to give piperazine-1,4-dicarboxylic acid tert-butyl ester 1-chloro-ethyl ester. A portion of piperazine-1,4-dicarboxylic acid tert-butyl ester 1-chloro-ethyl ester (682 mg, 1.67 mmol) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (201.4 mg, 0.327 mmol) in the presence of cesium carbonate (743.4 mg, 2.28 mmol) in dimethylformamide (7 mL) overnight to give 1-tert-butyl 4-(1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl)piperazine-1,4-dicarboxylate as an off-white lyophilized solid (259.9 mg, 91% yield). MS (ES+) m/z calcd. for $C_{34}H_{36}Cl_2F_2N_4O_4$: [(M+H)+]: 872, found: 872

EXAMPLE 13

Piperazine-1-carboxylic acid 1-(4-{[(2R,3S,4R,5S)-4-(4-chloro-2-fluoro-phenyl)-3-(3-chloro2-fluoro-phenyl)-4-cyano-5-(2,2-dimethyl-propyl)-pyrrolidine-2-carbonyl]-amino}-3-methoxy-benzoyloxy)-ethyl ester di-hydrochloride

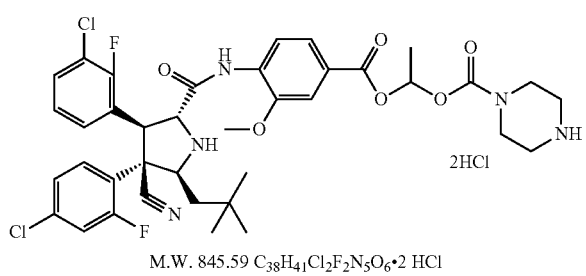 [SMILES: COc1cc(C(=O)OC(C)OC(=O)N2CCNCC2)ccc1NC(=O)[C@@H]1N[C@@H](CC(C)(C)C)[C@](C#N)(c2ccc(Cl)cc2F)[C@H]1c1cccc(Cl)c1F]

M.W. 845.59 $C_{38}H_{41}Cl_2F_2N_5O_6$·2 HCl

A solution of 1-tert-butyl 4-(1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl)piperazine-1,4-dicarboxylate (Example 12, 115.3 mg, 0.132 mmol) in methylene chloride (2 mL) was treated with a solution of hydrochloric acid in 1,4 dioxane (Sigma Aldrich, 4M, 0.33 mL, 1.32 mmol) over 5 min. The reaction mixture was stirred at room temperature for 90 min and concentrated to give piperazine-1-carboxylic acid 1-(4-{[(2R,3S,4R,5S)-4-(4-chloro-2-fluoro-phenyl)-3-(3-chloro2-fluoro-phenyl)-4-cyano-5-(2,2-dimethyl-propyl)-pyrrolidine-2-carbonyl]-amino}-3-methoxy-benzoyloxy)-ethyl ester di-hydrochloride as a white solid (119 mg, 100% yield). MS (ES+) m/z calcd. for $C_{38}H_{42}Cl_2F_2N_5O_6$: [(M+H)+]: 772, found: 772

EXAMPLE 14 rac-1,1-Dioxo-thiomorpholine-4-carboxylic acid 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester

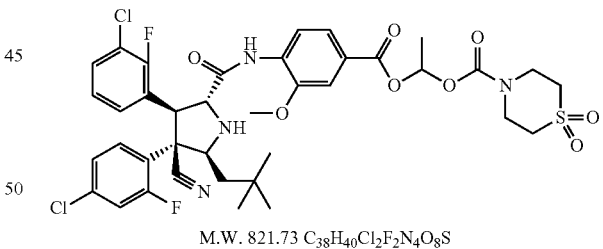

M.W. 821.73 $C_{38}H_{40}Cl_2F_2N_4O_8S$

In a manner similar to the method described in Example 3, 1-chloroethyl chloroformate (Oakwood, 1.32 g, 1 mL, 9.27 mmol) was reacted with thiomorpholine 1,1-dioxide (1.1638 g, 8.61 mmol) and pyridine (783 mg, 801 µl, 9.9 mmol) in methylene chloride (15 mL) at room temperature for 3 h to give 1,1-dioxo-thiomorpholine-4-carboxylic acid 1-chloroethyl ester. A portion of 1,1-dioxo-thiomorpholine-4-carboxylic acid 1-chloro-ethyl ester (577 mg, 1.614 mmol) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (150.5 mg, 0.244 mmol) in the presence of cesium carbonate (598.4 mg, 1.84 mmol) in dimethylformamide (7 mL) overnight to give 1,1-dioxo-thiomorpholine-4-carboxylic acid 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester as an off-white solid (175.3 mg, 87% yield). MS (ES$^+$) m/z calcd. for $C_{38}H_{41}Cl_2F_2N_4O_8S$: [(M+H)$^+$]: 821, found: 821

EXAMPLE 15

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,2-dimethyl-[1,3]dioxolan-4-ylmethylcarbamoyloxy)-ethyl ester

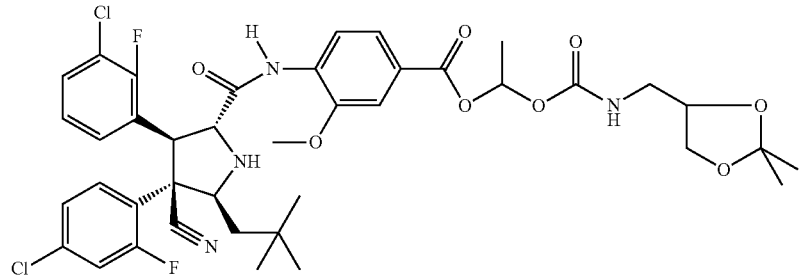

M.W. 817.72 $C_{40}H_{44}Cl_2F_2N_4O_8$

In a manner similar to the method described in Example 3, 1-chloroethyl chloroformate (1.46 g, 1.1 mL, 10.2 mmol) was reacted with (2,2-dimethyl-[1,3]-dioxolan-4-yl)-methylamine (Aldrich, 1.21 g, 1.2 mL, 8.98 mmol) and pyridine (870 mg, 0.89 mL, 11.0 mmol) in methylene chloride (15 mL) at 78° C. for 3 h to give 1-chloroethyl (2,2-dimethyl-1,3-dioxolan-4-yl)methylcarbamate with pyridine hydrochloride (1:1). A portion of this material (622 mg, 1.76 mmol) in dimethylformamide (5 mL) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (201 mg, 0.326 mmol) in the presence of cesium carbonate (806.9 mg, 2.48 mmol) in dimethylformamide (7 mL) overnight to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,2-dimethyl-[1,3]dioxolan-4-ylmethylcarbamoyloxy)-ethyl ester as a white solid (97.7 mg, 36% yield). MS (ES$^+$) m/z calcd. for $C_{40}H_{45}C_{12}F_2N_4O_8$: [(M+H)$^+$]: 817, found: 817

EXAMPLE 16

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,3-dihydroxy-propylcarbamoyloxy)-ethyl ester

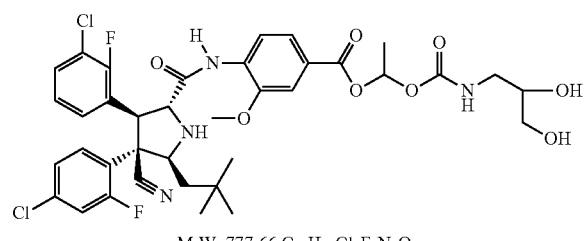

M.W. 777.66 $C_{37}H_{40}Cl_2F_2N_4O_8$

A solution of 1-((2,2-dimethyl-1,3-dioxolan-4-yl)methyl-carbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 15, 75.7 mg, 0.092 mmol) in acetonitrile (4 mL) was treated with a 2M solution of hydrochloric acid in ether (Sigma Aldrich, 0.5 mL, 1.00 mmol) and stirred for 70 min. The reaction mixture was concentrated, diluted with ethyl acetate and washed with saturated aqueous sodium bicarbonate, brine, dried and concentrated. The crude material was then purified by flash chromatography (methylene chloride/methanol) to give 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,3-dihydroxy-propylcarbamoyloxy)-ethyl ester as a white solid (36.6 mg, 50% yield). MS (ES$^+$) m/z calcd. for $C_{37}H_{40}Cl_2F_2N_4O_8$: [(M+H)$^+$]: 777 found: 777

EXAMPLE 17

1-(Tetrahydro-2H-pyran-4-ylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

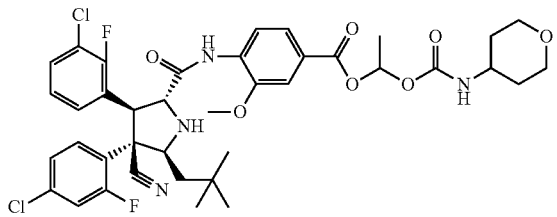

M.W. 787.69 $C_{39}H_{42}Cl_2F_2N_4O_7$

In a manner similar to the method described in Example 3, 1-chloroethyl chloroformate (Oakwood, 1.32 g, 1.0 mL, 9.27 mmol) was reacted with 4-aminotetrahydropyrane (Oakwood, 899 mg, 0.92 mL, 8.62 mmol) and pyridine (782 mg, 0.8 mL, 9.89 mmol) in methylene chloride (20 mL) at −78° C. for 3 h to give 1-chloroethyl tetrahydro-2H-pyran-4-ylcarbamate compound with pyridine hydrochloride (1:1). A portion of this material (520 mg, 1.61 mmol) in dimethylformamide (5 mL) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (151.4 mg, 0.246 mmol) and cesium carbonate (599.5 mg, 1.84 mmol) in dimethylformamide (4.00 mL) at room temperature for 17 h to give 1-(tetrahydro-2H-pyran-4-ylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid (145.7 mg, 75% yield). MS (ES$^+$) m/z calcd. for $C_{39}H_{42}Cl_2F_2N_4O_7$: [(M+H)$^+$]: 787, found: 787

EXAMPLE 18

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-{2-[2-(2-methoxy-ethoxy)-ethoxy]-ethoxycarbonyloxy}-ethyl ester

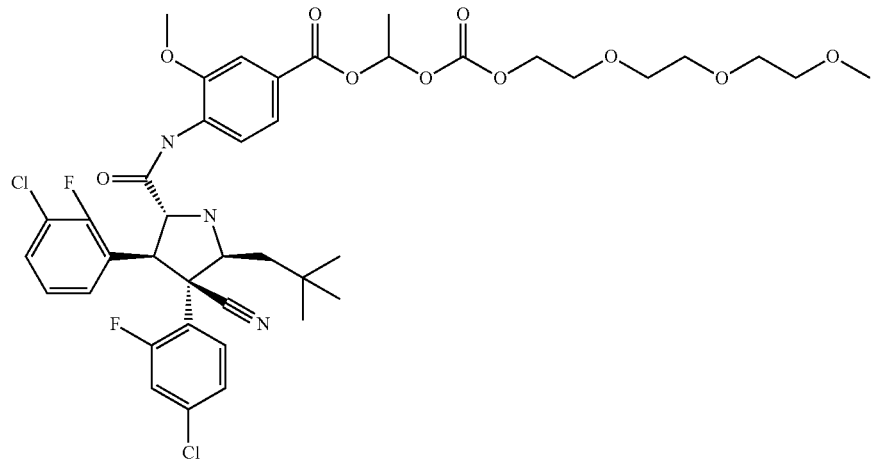

M.W. 850.75 C$_{41}$H$_{47}$Cl$_2$F$_2$N$_3$O$_{10}$

In a manner similar to the method described in Example 3, 1-chloroethyl chloroformate was reacted with 2-(2-(2-methoxyethoxy)ethoxy)ethanol (TCI) and pyridine in methylene chloride at −78° C. for 3 h to give 1-chloroethyl 2-(2-(2-methoxyethoxy)ethoxy)ethyl carbonate. This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-{2-[2-(2-methoxy-ethoxy)-ethoxy]-ethoxycarbonyloxy}-ethyl ester as a white solid. LCMS (ES$^+$) m/z calcd. for C$_{41}$H$_{48}$Cl$_2$F$_2$N$_3$O$_{10}$ [(M+H)$^+$]: 850, found: 850.

EXAMPLE 19

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-methoxy-ethoxy)-ethoxy]-ethoxy}-ethoxycarbonyloxy)-ethyl ester

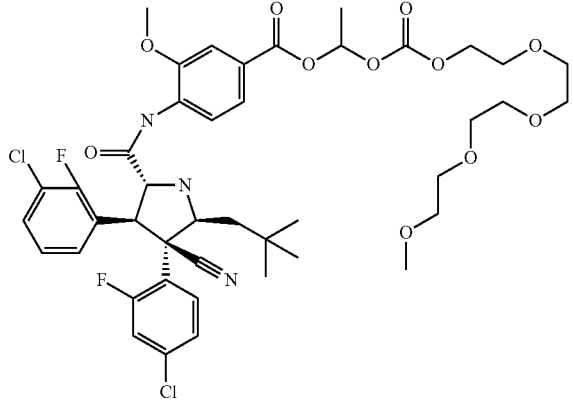

M.W. 894.80 C$_{43}$H$_{51}$Cl$_2$F$_2$N$_3$O$_{11}$

In a manner similar to the method described in Example 3, 1-chloroethyl chloroformate was reacted with 2,5,8,11-tetraoxamidecan-13-ol (TCI) and pyridine in methylene chloride at −78° C. for 3 h to give 1-chloroethyl 2,5,8,11-tetraoxamidecan-13-yl carbonate. This was then reacted with 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-methoxy-ethoxy)-ethoxy]-ethoxy}-ethoxycarbonyloxy)ethyl ester as a white solid. LCMS (ES$^+$) m/z calcd. for C$_{43}$H$_{52}$Cl$_2$F$_2$N$_3$O$_{11}$ [(M+H)$^+$]: 894, found: 894.

EXAMPLE 20

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[2-(2-{2-[2-(2-methoxy-ethoxy)-ethoxy]-ethoxy}-ethoxy)-ethoxycarbonyloxy]-ethyl ester

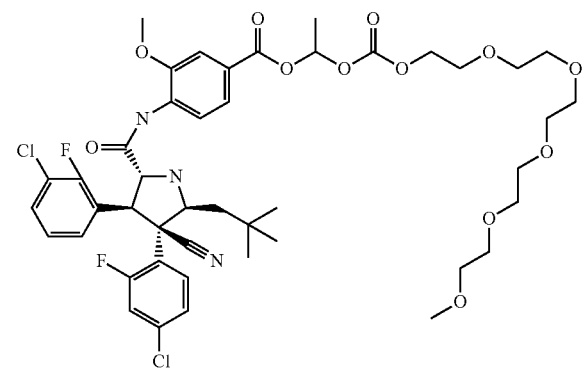

M.W. 938.86 C$_{45}$H$_{55}$Cl$_2$F$_2$N$_3$O$_{12}$

In a manner similar to the method described in Example 3, 1-chloroethyl chloroformate was reacted with pentaethylene glycol monomethyl ether (TCI) and pyridine in methylene chloride at −78° C. for 3 h to give 1-chloroethyl 2,5,8,11,14-pentaoxahexadecan-16-yl carbonate. This was then reacted with 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[2-(2-{2-[2-(2-methoxy-ethoxy)-ethoxy]-ethoxy}-ethoxy)-ethoxycarbonyloxy]-ethyl ester as a white solid. LCMS (ES$^+$) m/z calcd. for $C_{45}H_{56}Cl_2F_2N_3O_{12}$ [(M+H)$^+$]: 938, found: 938.

EXAMPLE 21

21-oxo-2,5,8,11,14,17,20,22-octaoxatetracosan-23-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

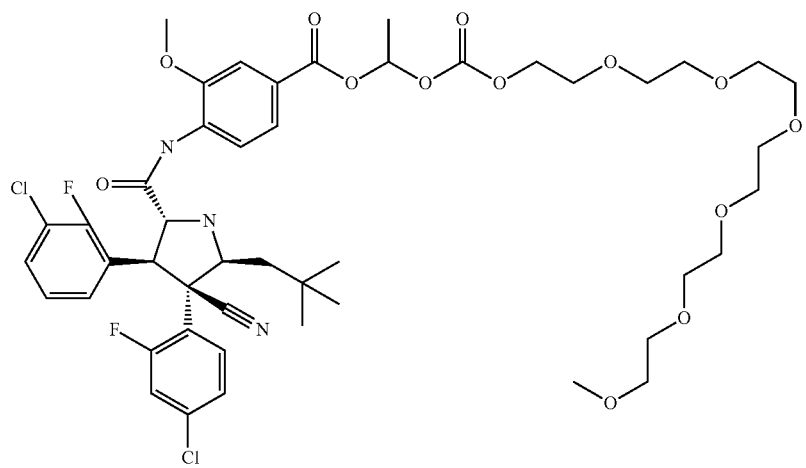

M.W. 982.91 $C_{47}H_{59}Cl_2F_2N_3O_{13}$

In a manner similar to the method described in Example 3, 1-chloroethyl chloroformate was reacted with 2,5,8,11,14,17-hexaoxanonadecan-19-ol (TCI) and pyridine in methylene chloride at −78° C. for 3 h to give 1-chloroethyl 2,5,8,11,14,17-hexaoxanonadecan-19-yl carbonate. This was then reacted with 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 21-oxo-2,5,8,11,14,17,20,22-octaoxatetracosan-23-yl-4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. LCMS (ES$^+$) m/z calcd. for $C_{47}H_{60}Cl_2F_2N_3O_{13}$ [(M+H)$^+$]: 982, found: 982.

EXAMPLE 22

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~750)

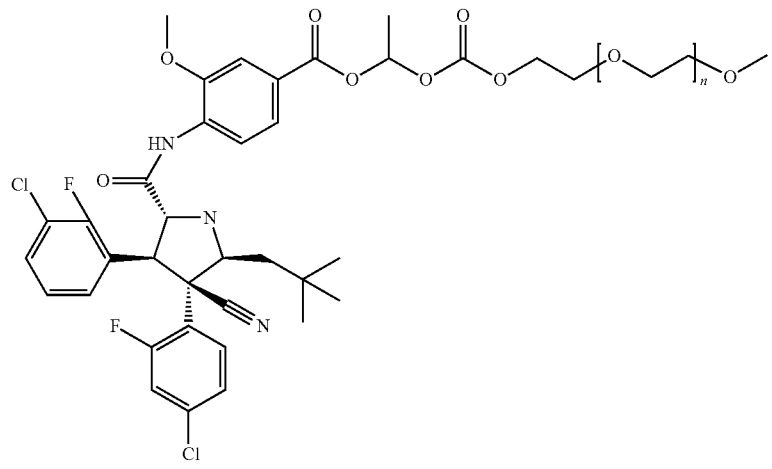

Average MW: 1438

In a manner similar to the method described in Example 3, 1-chloroethyl chloroformate was reacted with poly(ethylene glycol)monomethyl ether (mPEG) (Aldrich, average MW ~750) and pyridine in methylene chloride at −78° C. for 3 h to give the 1-chloroethyl mPEG carbonate. This 1-chloroethyl mPEG carbonate was then reacted with 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoic acid in the presence of cesium carbonate in dimethylformamide overnight to give, after high-performance liquid chromatography purification (10% to 100% acetonitrile in water), 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW ~750) as a waxy solid.

EXAMPLE 23

1-(2-(Benzyloxy)-2-oxoethylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

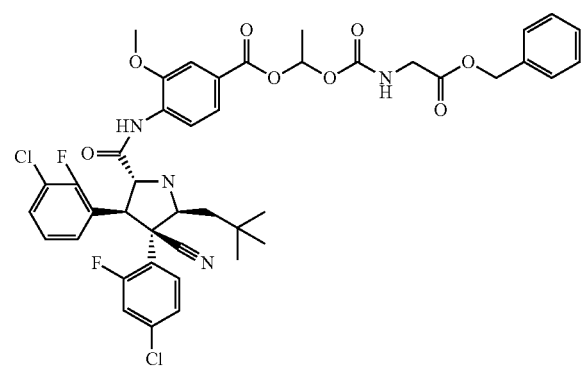

M.W. 851.74 $C_{43}H_{42}Cl_2F_2N_4O_8$

Benzyl 2-aminoacetate was generated from a treatment of benzyl 2-aminoacetate hydrochloride (Aldrich) in methylene chloride with aqueous sodium bicarbonate solution followed by water wash. To a cooled solution of benzyl 2-aminoacetate (1.837 g, 11.1 mmol) and pyridine (1.1 g, 1.1 mL, 13.9 mmol) in methylene chloride (17 mL) at −78° C., was added slowly 1-chloroethyl chloroformate (Aldrich, 1.67 g, 11.7 mmol) over ~10 min. The reaction mixture was allowed to stir at −78° C. for 3 h, giving a white precipitate. This cold reaction mixture was filtered to remove the solid and the filtrate was concentrated to dryness, giving the crude benzyl 2-((1-chloroethoxy)carbonylamino)acetate which was used for the next step without further purification.

To a solution of 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (215 mg, 0.349 mmol) in dimethylformamide (22 mL) was added cesium carbonate (2.15 g, 6.6 mmol). After stirring for 10 min, a solution of the freshly made benzyl 2-((1-chloroethoxy)carbonylamino)acetate (2.77 g crude, ~5.55 mmol) in dimethylformamide (5 mL) was added. The reaction mixture was allowed to stir at room temperature overnight. This reaction mixture was taken up in ethyl acetate, washed with water, brine and concentrated to dryness. The crude material was purified by flash chromatography (hexane/ethyl acetate, 90/10 to 10/90) to give 1-(2-(benzyloxy)-2-oxoethylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid (191 mg, 64% yield). LCMS (ES$^+$) m/z calcd. for $C_{43}H_{43}Cl_2F_2N_4O_8$ [(M+H)$^+$]: 851, found: 851.

EXAMPLE 24

2-((1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethoxy)carbonylamino)acetic acid

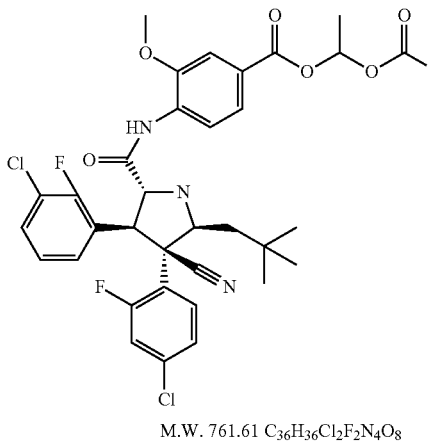

M.W. 761.61 $C_{36}H_{36}Cl_2F_2N_4O_8$

To a solution of 1-(2-(benzyloxy)-2-oxoethylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (Example 23, 35.8 mg, 0.042 mmol) in ethyl acetate (8 mL) was added 10% palladium on carbon (12 mg). The content was stirred at room temperature under 1 atm of hydrogen for 2 h. Palladium on carbon solids were filtered off and washed with ethyl acetate. The solution was concentrated to give 2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethoxy)carbonylamino)acetic acid as a white solid (20.6 mg, 61%)). MS (ES$^+$) m/z calcd. for $C_{36}H_{37}Cl_2F_2N_4O_8$ [(M+H)$^+$]: 761, found: 761.

EXAMPLE 25

(2S)-Dibenzyl 2-((1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethoxy)-carbonylamino)pentanedioate

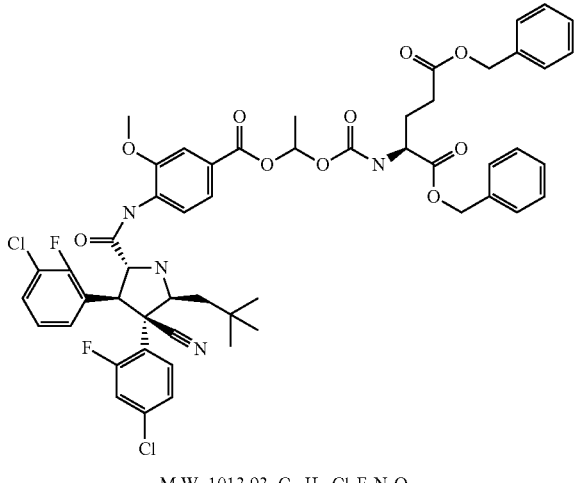

M.W. 1013.93, $C_{53}H_{52}Cl_2F_2N_4O_{10}$

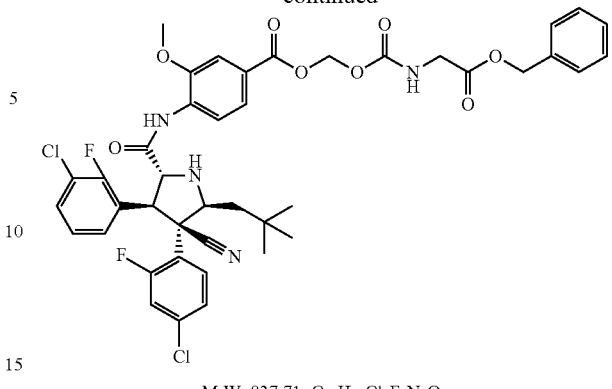

M.W. 837.71, $C_{42}H_{40}Cl_2F_2N_4O_8$

In a manner similar to the method described in Example 23, chloromethoxycarbonylamino-acetic acid benzyl ester was prepared from amino-acetic acid benzyl ester and 1-chloroethyl chloroformate (Aldrich) in the presence of pyridine in methylene chloride. It was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid and cesium carbonate in dimethylformamide to give chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid benzyloxycarbonylmethyl-carbamoyloxymethyl ester as a white solid. MS (ES$^+$) m/z calcd. for $C_{42}H_{41}Cl_2F_2N_4O_8$ [(M+H)$^+$]: 837, found: 837

EXAMPLE 30

2-(((4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)acetic acid

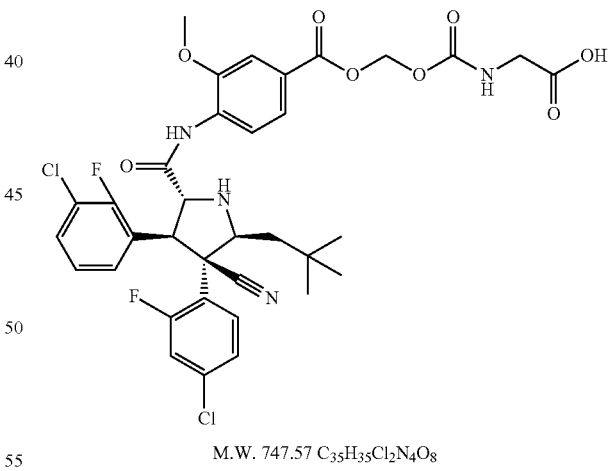

M.W. 747.57 $C_{35}H_{35}Cl_2N_4O_8$

In a manner similar to the method described in Example 24, a solution of 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid benzyloxycarbonylmethyl-carbamoyloxymethyl ester (Example 29) in ethyl acetate was treated with 10% palladium on carbon under 1 atm of hydrogen to give 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)-carbonylamino)acetic acid as a white solid. MS (ES$^+$) m/z calcd. for $C_{35}H_{36}Cl_2F_2N_4O_8$ [(M+H)$^+$]: 747, found: 747.

EXAMPLE 31

(S)-Dibenzyl 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)-pentanedioate

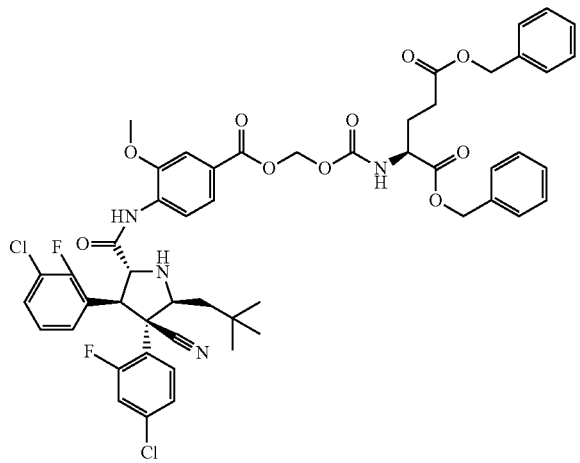

M.W. 999.88 $C_{52}H_{50}Cl_2F_2N_4O_{10}$

In a manner similar to the method described in Example 23, (S)-dibenzyl 2-((chloromethoxy)-carbonylamino)pentanedioate was prepared from (S)-dibenzyl 2-aminopentanedioate and chloromethyl chloroformate in the presence of pyridine in methylene chloride. It was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid and cesium carbonate in dimethylformamide to give chiral (S)-dibenzyl 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)-pentanedioate as a white solid. MS (ES$^+$) m/z calcd. for $C_{52}H_{51}Cl_2F_2N_4O_{10}$ [(M+H)$^+$]: 999, found: 999.

EXAMPLE 32

(S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)pentanedioic acid

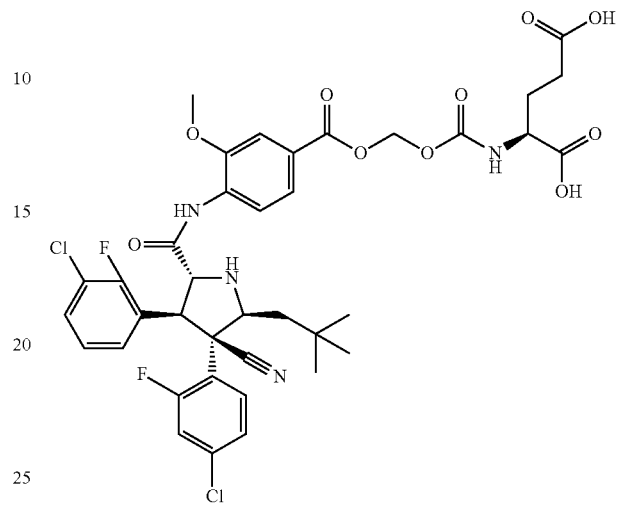

MW: 819.63 $C_{38}H_{38}Cl_2F_2N_4O_{10}$

In a manner similar to the method described in Example 24, a solution of chiral (S)-dibenzyl 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)pentanedioate (Example 31) in ethyl acetate was treated with 10% palladium on carbon under 1 atm of hydrogen to give chiral (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)-pentanedioic acid as a white solid. MS (ES$^+$) m/z calcd. for $C_{38}H_{39}Cl_2F_2N_4O_{10}$ [(M+H)$^+$]: 819, found: 819.

EXAMPLE 33

15-methyl-12-oxo-2,5,8,11,13-pentaoxahexadecan-14-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

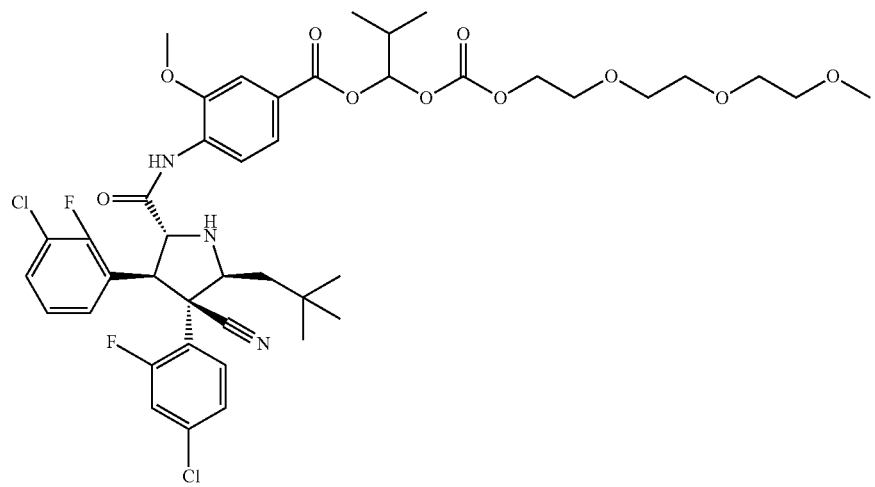

M.W. 878.8 $C_{43}H_{51}Cl_2F_2N_3O_{10}$

In a manner similar to the method described in Example 3, 1-chloro-2-methylpropyl chloroformate (Aldrich) was reacted with 2-(2-(2-methoxyethoxy)ethoxy)ethanol (TCI) and pyridine in methylene chloride at −78° C. for 3 h to give 1-chloro-2-methylpropyl 2-(2-(2-methoxyethoxy)-ethoxy) ethyl carbonate. This material was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 15-methyl-12-oxo-2,5,8,11,13-pentaoxahexadecan-14-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. MS (ES$^+$) m/z calcd. for $C_{43}H_{52}Cl_2F_2N_3O_{10}$: [(M+H)$^+$]: 878, found: 878.

EXAMPLE 34

3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

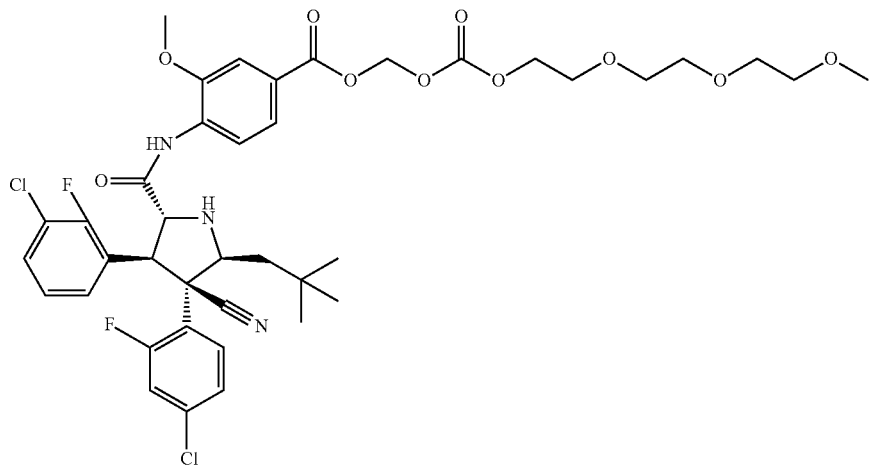

M.W. 836.72 $C_{40}H_{46}Cl_2F_2N_3O_{10}$

In a manner similar to the method described in Example 3, chloromethyl chloroformate (Aldrich) was reacted with 2-(2-(2-methoxyethoxy)ethoxy)ethanol (TCI) and pyridine in methylene chloride at −78° C. for 3 h to give chloromethyl 2-(2-(2-methoxyethoxy)ethoxy)ethyl carbonate. This material was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), chiral 3-oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. MS (ES$^+$) m/z calcd. for $C_{40}H_{47}Cl_2F_2N_3O_{10}$: [(M+H)$^+$]: 836, found: 836.

EXAMPLE 35

3-Oxo-2,4,7,10,13,16,19-heptaoxaicosyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate Chiral

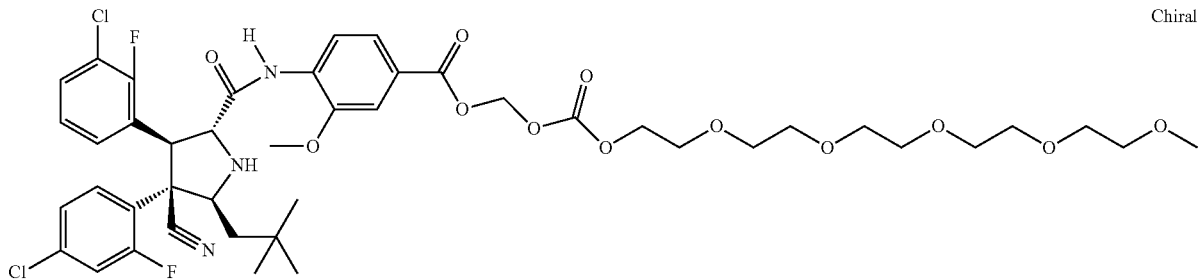

M.W. 924.83 $C_{44}H_{53}Cl_2F_2N_3O_{12}$

In a manner similar to the method described in Example 3, chloromethyl chloroformate (Aldrich) was reacted with pentaethylene glycol monomethyl ether (TCI) and pyridine in methylene chloride at −78° C. for 3 h to give chloromethyl 2,5,8,11,14-pentaoxahexadecan-16-yl carbonate. This material was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), chiral 3-oxo-2,4,7,10,13,16,19-heptaoxaicosyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. MS (ES+) m/z calcd. for $C_{44}H_{54}Cl_2F_2N_3O_{12}$: [(M+H)+]: 924, found: 924.

EXAMPLE 36

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester (mPEG, average MW, ~750)

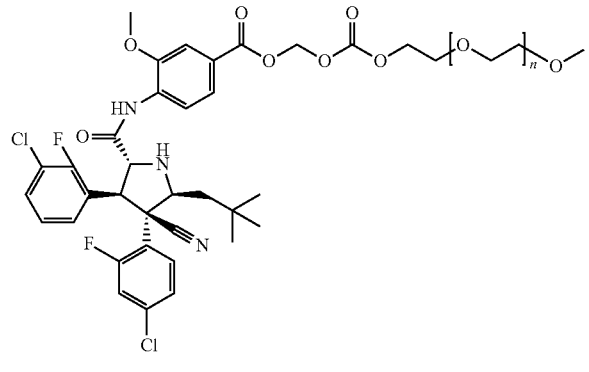

Average MW: ~1431

In a manner similar to the method described in Example 3, chloromethyl chloroformate (594 mg, 410 μl, 4.43 mmol) was reacted with poly(ethylene glycol)monomethyl ether (mPEG) (Aldrich, average MW ~750, 10.03 g, 13.4 mmol) and pyridine (1.32 g, 1.35 mL, 16.7 mmol) in methylene chloride (6 mL) at −78° C. for 3 h to give 1-chloromethyl mPEG carbonate with pyridine hydrochloride (1:1). This 1-chloromethyl mPEG carbonate (4.67 g, 4.87 mmol) in dimethylformamide (18 mL) was then reacted with 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (300 mg, 0.487 mmol) and cesium carbonate (1.92 g, 5.89 mmol) in dimethylformamide (7 mL) overnight to give, after high-performance liquid chromatography purification (10% to 100% acetonitrile in water), chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester (mPEG, average MW, ~750) as a waxy solid (586.3 mg, 84.5% yield).

EXAMPLE 37

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (average MW, ~2695)

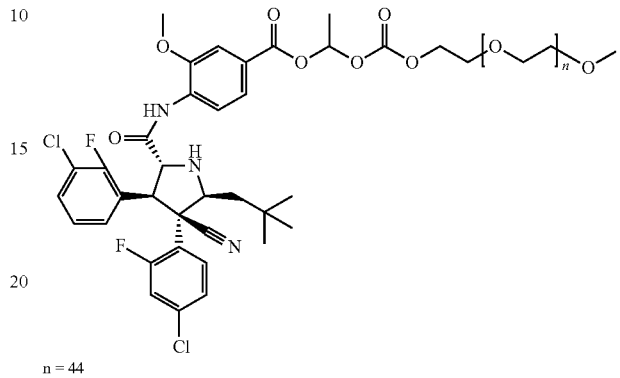

n = 44

In a manner similar to the method described in Example 3, chloroethyl chloroformate (Oakwood, 1.46 g, 1.1 mL, 10.2 mmol) was reacted with poly(ethylene glycol)monomethyl ether (mPEG) (Aldrich, average MW ~2000, 18.84 g, 9.42 mmol) and pyridine (939 mg, 0.96 mL, 11.9 mmol) in methylene chloride (6 mL) at −78° C. for 3 h to give 1-chloroethyl mPEG carbonate with pyridine hydrochloride (1:1). This 1-chloroethyl mPEG carbonate (4.67 g, 4.87 mmol) in dimethylformamide (25 mL) was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (300 mg, 0.487 mmol) and cesium carbonate (1.97 g, 6.04 mmol) in dimethylformamide (6 mL) overnight to give, after high-performance liquid chromatography purification (10% to 100% acetonitrile in water), 4-{[(2R,3S,4R,5S)-3-(3-chloro-2-fluoro-phenyl)-4-(4-chloro-2-fluoro-phenyl)-4-cyano-5-(2,2-dimethyl-propyl)pyrrolidine-2-carbonyl]-amino}-3-methoxy-benzoic acid 1-mPEG-carbonyloxy-ethyl ester, Average MW: ~2695 (mPEG, average MW, ~2000) as a white solid (171.6 mg, 13% yield).

EXAMPLE 37A

1-Chloroethyl 2-methoxyethyl carbonate-mPEG (average MW ~2300)

Methoxy-poly(ethylene glycol) (ID Biochem, average MW ~2200 determined by MALDI-TOF MS, 2.5 kg, ~1.14 mol) and lithium carbonate (185 g, 2.5 mol) were charged to a 50-L glass reactor, and dichloromethane (39.8 kg, 30.0 L) was added. The mixture was stirred for 1 hour, and then 1-chloroethyl chloroformate (1.07 kg, 819 mL, 7.5 mol) was added via dropping funnel. With vigorous mixing, a catalytic amount of pyridine (4.94 g, 5.05 mL, 62.5 mmol) was added, and gas evolution was observed. The mixture was stirred at 25° C. under $N_2$ for 21 hours. HPLC-CAD analysis showed ~3% mPEG-OH remaining. The reaction mixture was filtered to remove insoluble salts, and then the liquors were polish filtered through a 0.4 micron filter. The liquors were concentrated to remove dichloromethane by vacuum distillation and the solvent exchanged to n-heptane. The resulting slurry in n-heptane was cooled to 0° C. and aged for 1 hour prior to filtering the product as a white powder. The solids were washed with n-heptane then dried at 35° C. in a vacuum oven with N₂ purge to yield 2340 g (90%) of 1-chloroethyl 2-methoxyethyl carbonate-mPEG (average MW ~2300).

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200) (Average MW: ~2900)

A 12-L flask was charged with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoic acid cesium salt (400 g, 533 mmol), 1-chloroethyl 2-methoxyethyl carbonate-mPEG, (avg MW~2300) (1.51 kg, ~657 mmol), and cesium carbonate (43.4 g, 133 mmol, Eq: 0.25), followed by DMSO (4.00 L). The mixture was stirred and heated to 50° C. for 4 hours. The temperature was adjusted to 30° C. and the reaction stirred for 6 days. Additional 1-chloroethyl 2-methoxyethyl carbonate-mPEG, avg MW ~2300) (112 g, ~49 mmol) was added, and the mixture heated again to 50° C. for 2 days. HPLC analysis showed ca. 98% conversion. The reaction mixture was cooled to 20° C., then poured into a prepared solution containing water (8.00 L) and hydrochloric acid (26.7 ml, 320 mmol). The resulting solution was stirred for a few minutes, and then the pH adjusted to ~6.5 by addition of Cs₂CO₃. The solution was stirred until analysis (HPLC-CAD) showed complete hydrolysis of excess 1-chloroethyl 2-methoxyethyl carbonate-mPEG to methoxy-poly(ethylene glycol). The solution was extracted with dichloromethane (10.6 kg, 8.00 L). The dichloromethane fraction was washed with water (8.00 kg, 8.00 L) four (4) times, and then with brine. The organic phase was concentrated under vacuum to give 1.885 kg crude pasty-solid that contained a mixture of the product and mPEG-OH. This residue was dissolved in isopropyl acetate (26.1 kg, 30.0 L) and then washed with 50% brine solution (1.13 L, prepared from 200 g NaCl in 1.13 L water). The mixture was allowed to settle for 1 h, and then the lower aqueous phase was removed. The remaining isopropyl acetate organic phase was polish filtered through diatomaceous earth. This solution was concentrated by vacuum distillation to provide a solid residue that was re-dissolved in isopropyl acetate (4.0 L). Once a clear solution was achieved, it was cooled to 10° C. and then n-heptane (8.0 L) was slowly added with vigorous mixing.

After the first ca. 1.0 L was added, the product began to precipitate as a fine, white slurry.

EXAMPLE 38

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester (mPEG, average MW, ~2000)

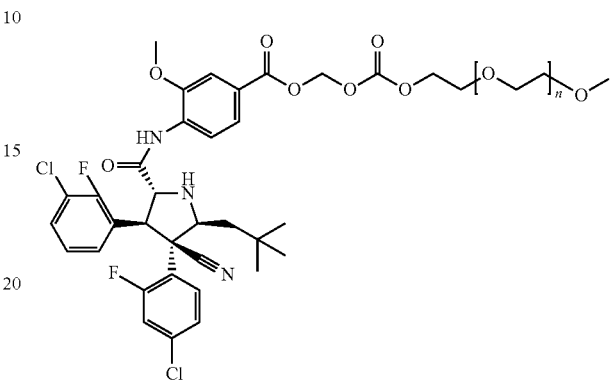

Average MW: ~2674

In a manner similar to the method described in Example 3, chloromethyl chloroformate (Oakwood) was reacted with poly(ethylene glycol)monomethyl ether (mPEG) (Aldrich, average MW ~2000) and pyridine in methylene chloride at −78° C. for 3 h to give 1-chloromethyl mPEG. This 1-chloromethyl mPEG carbonate was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid and cesium carbonate in dimethylformamide overnight to give, after high-performance liquid chromatography purification (10% to 100% acetonitrile in water), chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester (mPEG, average MW, ~2000) as a white solid.

EXAMPLE 39

3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

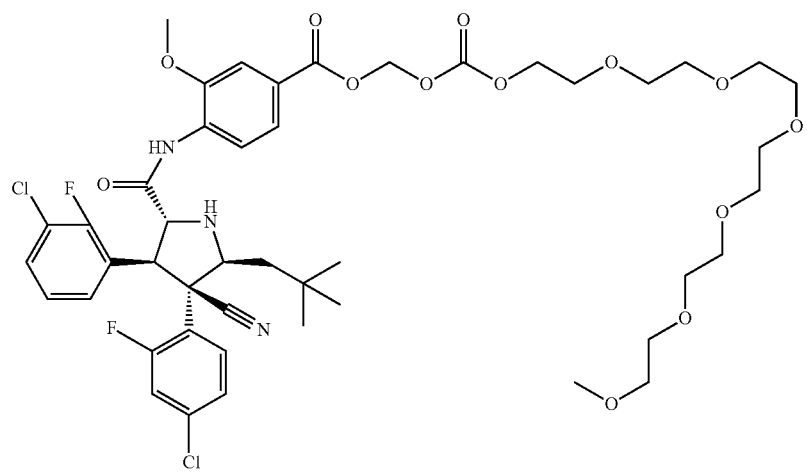

M.W. 968.88 C₄₆H₅₇Cl₂F₂N₃O₁₃

In a manner similar to the method described in Example 3, chloromethyl chloroformate (Aldrich) was reacted with 2,5,8,11,14,17-hexaoxanonadecan-19-ol (TCI) and pyridine in methylene chloride at −78° C. for 3 h to give chloromethyl 2,5,8,11,14,17-hexaoxanonadecan-19-yl carbonate. This material was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), chiral-3-oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. MS (ES$^+$) m/z calcd. for $C_{46}H_{58}Cl_2F_2N_3O_{13}$: [(M+H)$^+$]: 968, found: 968.

EXAMPLE 40

27-Oxo-2,5,8,11,14,17,20,23,26,28-decaoxatriacontan-29-yl-4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

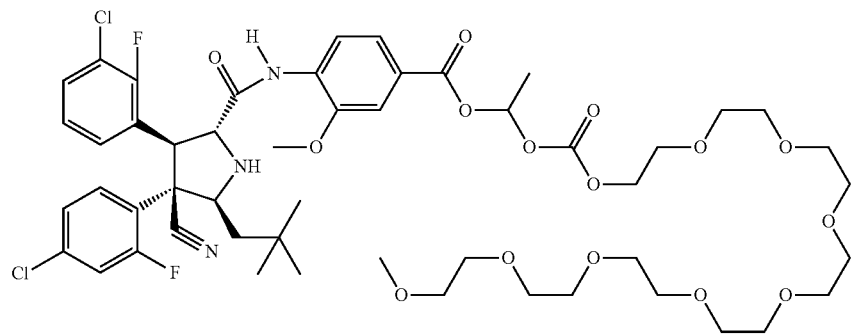

M.W. 1071.02 $C_{51}H_{67}Cl_2F_2N_3O_{15}$

In a manner similar to the method described in Example 3, 1-chloroethyl chloroformate (Aldrich) was reacted with octaethylene glycol monomethyl ether (TCI) and pyridine in methylene chloride at −78° C. for 3 h to give 1-chloroethyl 2,5,8,11,14,17,20,23-octaoxapentacosan-25-yl carbonate. This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification (hexane/ethyl acetate, 80/20 to 20/80), 27-oxo-2,5,8,11,14,17,20,23,26,28-decaoxatriacontan-29-yl-4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. MS (ES$^+$) m/z calcd. for $C_{51}H_{68}Cl_2F_2N_3O_{15}$: [(M+H)$^+$]: 1071, found: 1070.

EXAMPLE 41

24-Oxo-2,5,8,11,14,17,20,23,25-nonaoxaheptacosan-26-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

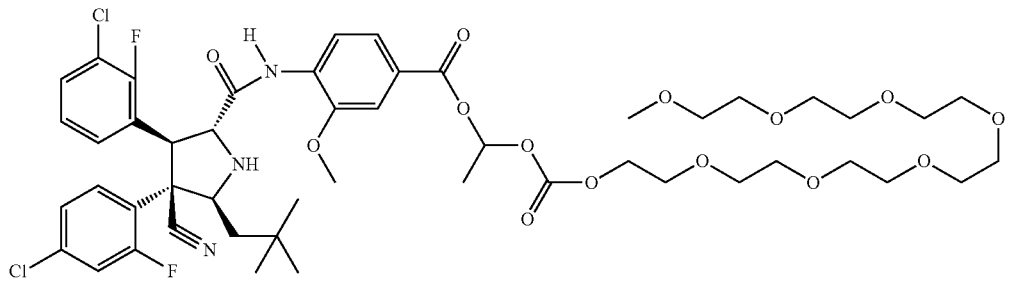

M.W. 1071.02 $C_{51}H_{67}Cl_2F_2N_3O_{15}$

In a manner similar to the method described in Example 3, 1-chloroethyl chloroformate (Aldrich) was reacted with heptaethylene glycol monomethyl ether (TCI) and pyridine in methylene chloride at −78° C. for 3 h to give 1-chloroethyl 2,5,8,11,14,17,20,23-octaoxapentacosan-25-yl carbonate. This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoic acid in the presence of cesium carbonate in dimethylformamide overnight to give, after flash chromatography purification (hexane/ethyl acetate, 80/20 to 20/80), 24-oxo-2,5,8,11,14,17,20,23,25-nonaoxaheptacosan-26-yl-4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid. MS (ES+) m/z calcd. for $C_{51}H_{68}Cl_2F_2N_3O_{15}$: [(M+H)+]: 1026, found: 1026.

EXAMPLE 42

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide (mPEG-NH$_2$, average MW, ~550)

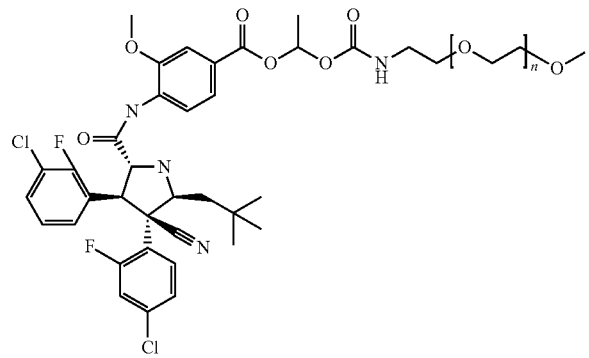

Average MW: ~1240

In a manner similar to the method described in Example 3, 1-chloroethyl chloroformate (Oakwood) was reacted with poly(ethylene glycol)mono amino mono methyl ether (mPEG-NH$_2$, average MW, ~550, LaySan Bio Inc) and pyridine in methylene chloride at −78° C. for 3 h to give 1-chloroethyl mPEG-NH$_2$ carbamate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoic acid in the presence of cesium carbonate in dimethylformamide overnight to give, after by high-performance liquid chromatography purification (acetonitrile/water), 4-{[(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide (mPEG, average MW, ~550) as a light brown solid.

EXAMPLE 43

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide (mPEG-NH$_2$, average MW, ~1000)

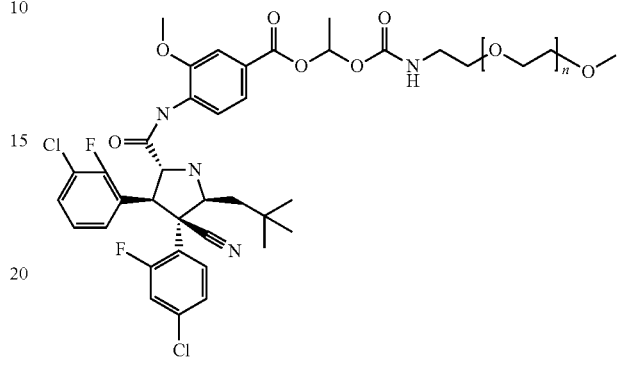

Average MW: ~1687

In a manner similar to the method described in Example 3, 1-chloroethyl chloroformate (Oakwood) was reacted with poly(ethylene glycol)mono amino mono methyl ether (mPEG-NH$_2$, average MW, ~1000, LaySan Bio Inc.) and pyridine in methylene chloride at −78° C. for 3 h to give 1-chloroethyl mPEG-NH$_2$ carbamate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after by high-performance liquid chromatography purification (acetonitrile/water), 4-{[(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide (mPEG-NH$_2$, average MW ~1000) as a light brown solid.

EXAMPLE 44

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide (mPEG-NH$_2$, average MW, ~2000)

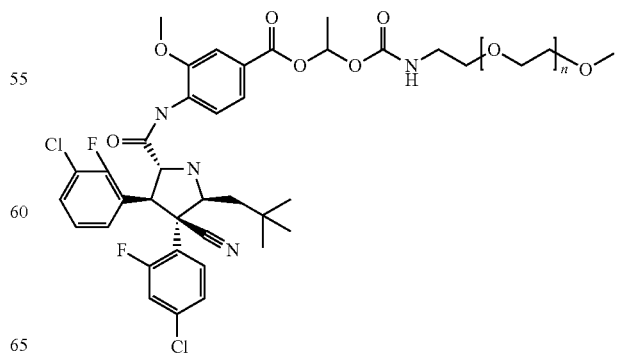

Average MW: ~2687

In a manner similar to the method described in Example 3, 1-chloroethyl chloroformate (Oakwood) was reacted with poly(ethylene glycol)mono amino mono methyl ether (mPEG-NH$_2$, average MW, ~2000, LaySan Bio Inc.) and pyridine in methylene chloride at −78° C. for 3 h to give 1-chloroethyl mPEG-NH$_2$ carbamate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after by high-performance liquid chromatography purification (acetonitrile/water), 4-{[(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide (mPEG-NH$_2$, average MW, ~2000) as a white solid.

EXAMPLE 45

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide (mPEG-NH$_2$, average MW ~2000)

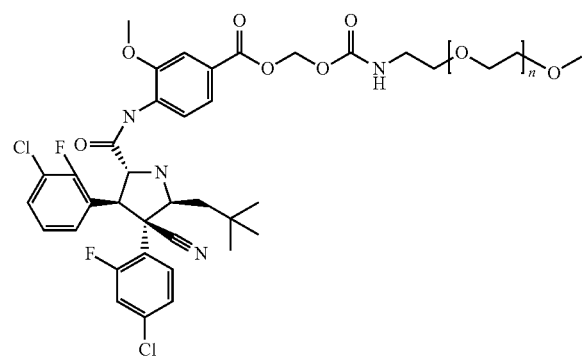

Average MW: ~2673

In a manner similar to the method described in Example 3, chloromethyl chloroformate (Oakwood) was reacted with poly(ethylene glycol)mono amino mono methyl ether (mPEG-NH$_2$, average MW ~2000, LaySan Bio Inc.) and pyridine in methylene chloride at −78° C. for 3 h to give 1-chloromethyl mPEG-NH$_2$ carbamate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after by high-performance liquid chromatography purification (acetonitrile/water), chiral 4-{[(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide (mPEG-NH$_2$, average MW 2000) as a white solid.

EXAMPLE 46

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide (mPEG-NH$_2$, average MW ~1000)

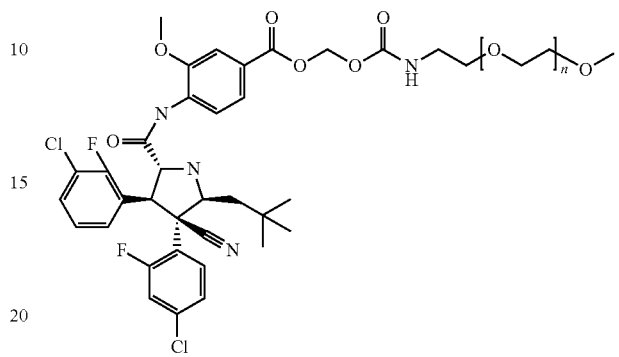

Average MW: ~1673

In a manner similar to the method described in Example 3, chloromethyl chloroformate (Oakwood, (160 mg, 110 μl, 1.24 mmol)) was reacted with poly(ethylene glycol)mono amino mono methyl ether (mPEG-NH$_2$, average MW ~1000, LaySan Bio Inc.) (999.8 mg, 1.00 mmol) and pyridine (53.8 mg, 0.055 mL, 0.68 mmol) in the presence of molecular sieves (~1.74 g, microwave dried, 8-12 mesh) in methylene chloride at −78° C. for 3 h to give 1-chloromethyl mPEG-NH$_2$ carbamate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (124 mg, 0.201 mmol) and cesium carbonate (467.3 mg, 1.43 mmol) in dimethylformamide (8 mL) overnight to give, after by high-performance liquid chromatography purification (acetonitrile/water), chiral-4-{[(2R,3S,4R,5S)-3-(3-chloro-2-fluoro-phenyl)-4-(4-chloro-2-fluoro-phenyl)-4-cyano-5-(2,2-dimethyl-propyl)pyrrolidine-2-carbonyl]-amino}-3-methoxy-benzoic acid 1-mPEG-carbonyloxy-methyl amide (mPEG-NH$_2$, average MW ~1000) as a white solid (258 mg, 76% yield).

EXAMPLE 47

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide (mPEG-NH$_2$, average MW ~550)

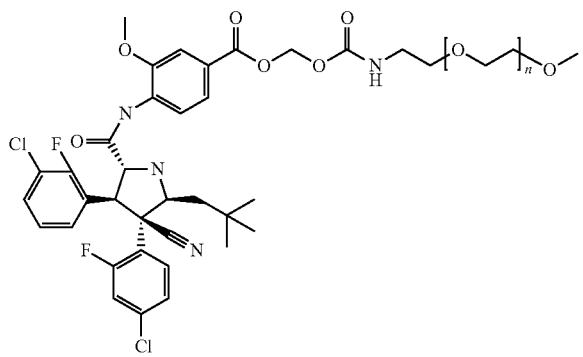

Average MW: ~1223

In a manner similar to the method described in Example 46, chloromethyl chloroformate (Oakwood, 167 mg, 0.11 mL, 1.29 mmol) was reacted with poly(ethylene glycol)mono amino mono methyl ether (mPEG-NH$_2$, average MW ~550, LaySan Bio Inc.) (576.4 mg, 1.05 mmol) and pyridine (117 mg, 0.12 mL, 1.48 mmol) in the presence of molecular sieves (~0.5 g, microwave dried, 8-12 mesh) in methylene chloride at −78° C. for 3 h to give 1-chloromethyl mPEG-NH$_2$ carbamate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (130.4 mg, 0.212 mmol) and cesium carbonate (479 mg, 1.47 mmol) in dimethylformamide (8 mL) overnight to give, after by high-performance liquid chromatography purification (acetonitrile/water), chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide (mPEG-NH$_2$, average MW, ~550) as a white solid (173.2 mg, 67.0% yield).

EXAMPLE 48

(S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)propanoic acid

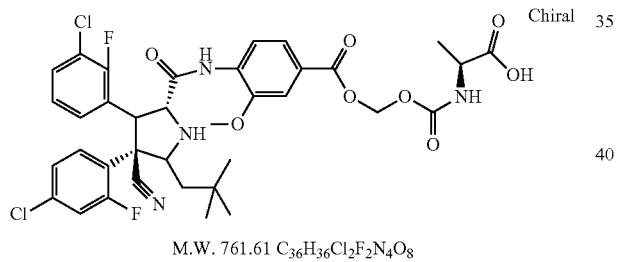

M.W. 761.61 C$_{36}$H$_{36}$Cl$_2$F$_2$N$_4$O$_8$

In a manner similar to the method described in Example 23, (S)-benzyl 2-((chloromethoxy)-carbonylamino)propanoate was prepared from (S)-benzyl 2-aminopropanoate (Chem-Impex) and 1-chloromethyl chloroformate (Aldrich) in the presence of pyridine in methylene chloride. It was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid and cesium carbonate in dimethylformamide to give chiral ((S)-1-(benzyloxy)-1-oxopropan-2-ylcarbamoyloxy)methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate as a white solid.

In a manner similar to the method described in Example 24, a solution of chiral ((S)-1-(benzyloxy)-1-oxopropan-2-ylcarbamoyloxy)methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate in ethyl acetate was treated with 10% palladium on carbon under 1 atm of hydrogen to give chiral (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)propanoic acid as a white solid. MS (ES$^+$) m/z calcd. for C$_{36}$H$_{36}$Cl$_2$F$_2$N$_4$O$_8$: [(M+H)$^+$]: 761, found: 761.

EXAMPLE 49

Dibenzyl 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester

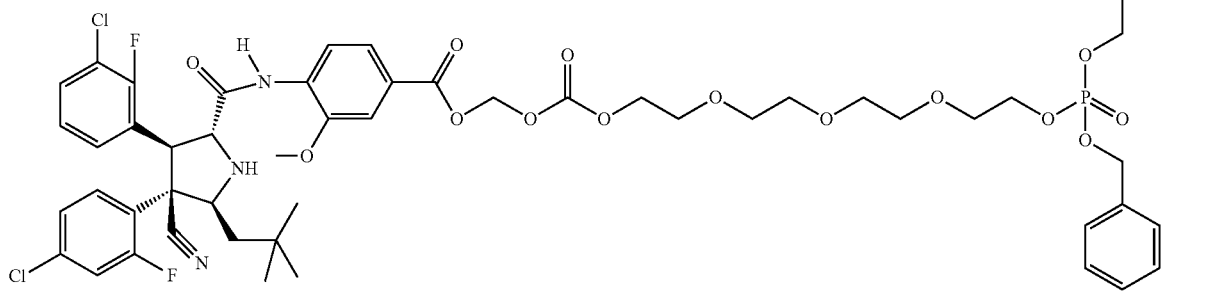

M.W. 1126.98 C$_{55}$H$_{60}$Cl$_2$F$_2$N$_3$O$_{14}$P

In a manner similar to the method described in Example 3, chloromethyl chloroformate (Oakwood) was reacted with dibenzyl 2-(2-(2-(2-hydroxyethoxy)ethoxy)ethoxy)ethyl phosphate (Example 54) and pyridine in methylene chloride at −78° C. for 3 h to give the corresponding chloromethyl carbonate with pyridine hydrochloride (1:1). This was then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid in the presence of cesium carbonate in dimethylformamide overnight to give, after flash chromatography purification, chiral dibenzyl 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester. MS (ES+) m/z calcd. for $C_{55}H_{61}Cl_2F_2N_3O_{14}P$: [(M+H)+]: 1126, found: 1126.

EXAMPLE 50

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester

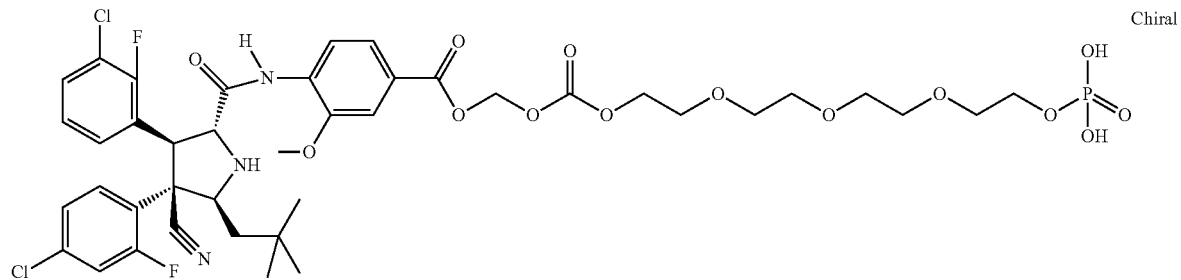

M.W. 946.73 $C_{41}H_{48}Cl_2F_2N_3O_{14}P$

A solution of chiral dibenzyl 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester (Example 49, 106.7 mg, 0.095 mmol) in ethyl acetate (10 mL) was treated with 10% palladium on carbon (58 mg) under 1 atm of hydrogen for 1 h. The reaction mixture was filtrated and the filtrate was concentrated to give chiral 4-{[(2R,3S,4R,5S)-4-(4-chloro-2-fluoro-phenyl)-3-(3-chloro-2-fluoro-phenyl)-4-cyano-5-(2,2-dimethyl-propyl)pyrrolidine-2-carbonyl]-amino}-3-methoxy-benzoic acid 2-{2-[2-(2-phosphonooxy-ethoxy)ethoxy]-ethoxy}-ethoxycarbonyloxymethyl ester as a white solid (75 mg, 82% yield). MS (ES+) m/z calcd. for $C_{41}H_{49}Cl_2F_2N_3O_{14}P$: [(M+H)+]: 946, found: 946.

EXAMPLE 51

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid phosphonooxymethyl ester; compound with trifluoro-acetic acid

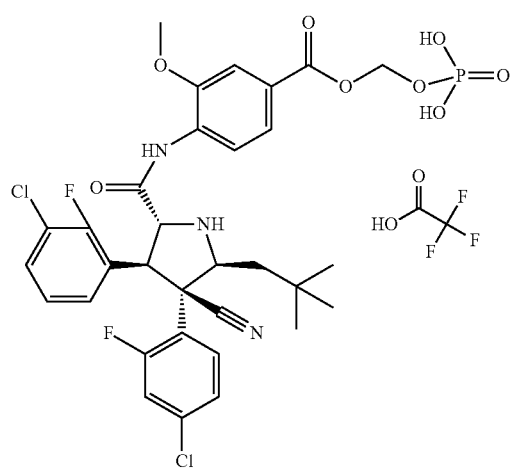

M.W. 840.51 $C_{32}H_{32}Cl_2F_2N_3O_8P \cdot C_2F_3O_2H$

In a 25 mL pear-shaped flask, (di-tert-butoxyphosphoryloxy)methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (20 mg, 23.8 μmmol, Example 2) was combined with dichloromethane (1 mL) to give a colorless solution which was cooled in an ice-water bath. After 5 min trifluoroacetic acid (744 mg, 0.5 mL, 6.53 mmol) was added over 8 min. The reaction mixture was concentrated and dried in vacuo overnight to give 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid phosphonooxymethyl ester, trifluoro-acetate salt, as off-white solids (19.5 mg, 97%).

EXAMPLE 52

1-(((3aR,5R,6S,6aR)-5-((R)-2,2-dimethyl-1,3-dioxolan-4-yl)-2,2-dimethyltetrahydrofuro[3,2-d][1,3]dioxol-6-yloxy)carbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate

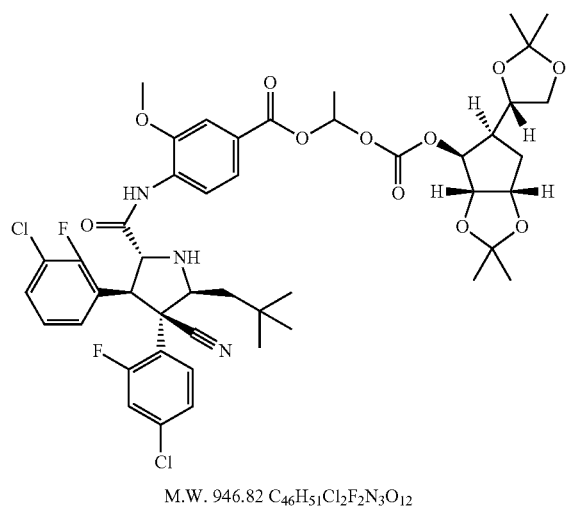 [SMILES: COc1cc(C(=O)OC(C)OC(=O)O[C@H]2[C@@H]([C@H]3COC(C)(C)O3)C[C@@H]3OC(C)(C)O[C@H]23)ccc1NC(=O)[C@@H]1N[C@@H](CC(C)(C)C)[C@](C#N)(c2ccc(Cl)cc2F)[C@H]1c1cccc(Cl)c1F]

M.W. 946.82 $C_{46}H_{51}Cl_2F_2N_3O_{12}$

To a solution of diacetone-D-glucose (1.56 g, 6 mmol) and pyridine (1.09 g, 1.12 mL, 13.8 mmol) in methylene chloride (6 mL) at −78° C. was added slowly a solution of 1-chloroethyl chloroformate (970 mg, 732 μl, 6.78 mmol) in methylene chloride (4 mL). After addition, the reaction mixture was allowed to stir at −78° C. for 1.5 h. Then the cold bath was removed and the reaction mixture was warmed up to room temperature. The reaction mixture was concentrated in vacuo and taken up in diethyl ether. The precipitate was filtered and the solid was washed thoroughly with diethyl ether. The filtrate and washing solutions were combined and concentrated to give 2.135 g of 1-chloroethyl (3aS,5S,6R,6aS)-5-((S)-2,2-dimethyl-1,3-dioxolan-4-yl)-2,2-dimethyltetrahydrofuro[3,2-d][1,3]dioxol-6-yl carbonate as clear light yellow thick oil, which was used directly without further purification.

To a solution of 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 100 mg, 162 μmol) in dry dimethyl formamide (4 mL) was added cesium carbonate (185 mg, 568 μmol). The mixture was stirred for 10 min at room temperature. The freshly made solution of 1-chloroethyl (3aS,5S,6R,6aS)-5-((S)-2,2-dimethyl-1,3-dioxolan-4-yl)-2,2-dimethyltetrahydrofuro[3,2-d][1,3]dioxol-6-yl carbonate (178 mg, 487 μmol) in 4 mL of dry dimethyl formamide was added to the above mixture and stirred at room temperature overnight. It was diluted with ethyl acetate and washed with water (2×) and brine. The organic layer was dried over anhydrous sodium sulfate, filtered and concentrated to give a crude, which was purified with flash chromatography (0-50% ethyl acetate in hexane over 25 min) to give an off-white solid (127 mg, 82% yield). LCMS (ES+) m/z calcd. for $C_{46}H_{51}Cl_2F_2N_3O_{12}$ [(M+H)+]: 946, found: 946.

EXAMPLE 53

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[(2R,3R,4R,5S)-2-((R)-1,2-dihydroxy-ethyl)-4,5-dihydroxy-tetrahydro-furan-3-yloxycarbonyloxy]-ethyl ester

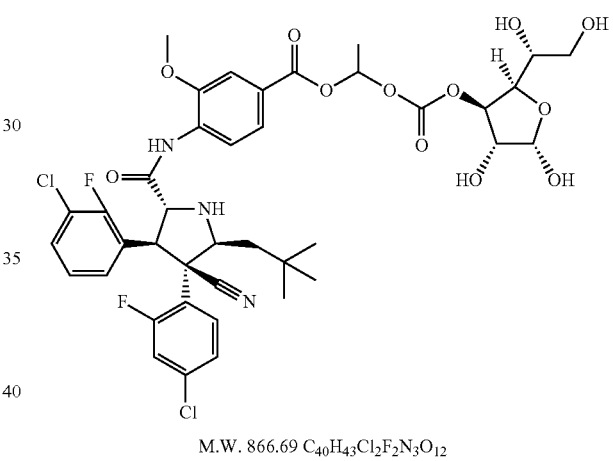

M.W. 866.69 $C_{40}H_{43}Cl_2F_2N_3O_{12}$

In a 15 mL round-bottomed flask was charged with 1-(((3aR,5R,6S,6aR)-5-((R)-2,2-dimethyl-1,3-dioxolan-4-yl)-2,2-dimethyltetrahydrofuro[3,2-d][1,3]dioxol-6-yloxy)carbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (111 mg, 117 μmol). The mix of trifluoroacetic acid (1.48 g, 1 mL, 13.0 mmol) and water (375 mg, 375 μl, 20.8 mmol) was added. LC-MS indicated the completion of the reaction after stirring at room temperature for 1 h.

The reaction mixture was concentrated in vacuo, and the residue was reconstituted with ethyl acetate. It was washed with water (2×) and brine. The ethyl acetate layer was separated and dried over anhydrous sodium sulfate, then filtered. The filtrate was concentrated to give a crude, which was purified with flash chromatography (24 pre-packed silica gel column, eluted with ethyl acetate over 20 min) to yield a white solid (24 mg, 23% yield). LCMS (ES+) m/z calcd. for $C_{40}H_{43}Cl_2F_2N_3O_{12}$ [(M+H)+]: 866, found: 866.

EXAMPLE 54

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-dibenzyloxyphosphoryloxy-ethoxy)-ethoxy]-ethoxy}-ethoxycarbonyloxy)-ethyl ester

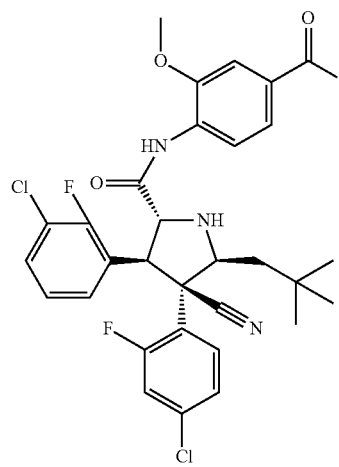
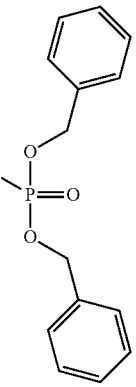

M.W. 1140.99 $C_{56}H_{62}Cl_2F_2N_3O_{14}P$

In a 100 mL three-necked flask equipped with Argon inlet, a solution of potassium t-butoxide (750 mg, 6.69 mmol) in tetrahydrofuran (3 mL) was added to the tetraethylene glycol (5.41 g, 4.81 mL, 27.9 mmol) in anhydrous tetrahydrofuran (30 mL) at room temperature. The mixture was stirred at room temperature for 20 min. It was cooled down to −40° C. A solution of tetrabenzyl pyrophosphate (3000 mg, 5.57 mmol) in tetrahydrofuran (20 mL) was added to the above cold mixture through a syringe. The reaction mixture was kept stirring at −40° C. for 5 min. LC-MS analysis of the reaction mixture showed a lot of unreacted tetrabenzyl pyrophosphate, and no improvement was observed after 30 min. Another fresh portion of the mixture of tetraethylene glycol and potassium tert-butoxide in tetrahydrofuran (same amounts, repeated the procedure as aforementioned) was added to the reaction mixture at −40° C. Tetrabenzyl pyrophosphate peak disappeared after 5 min. Acetic acid (5 eq) was added to quench the reaction at −40° C. The reaction mixture was warmed up to room temperature and concentrated in vacuo. The residue was reconstituted with ethyl acetate. It was washed with water (2×) and brine. The ethyl acetate layer was dried over anhydrous sodium sulfate. The solids were filtered off, and the filtrate was concentrated to give a crude, which was purified with flash column (80 g pre-packed silica gel column, eluted with 0-10% methanol in ethyl acetate) to give 1.14 g of dibenzyl 2-(2-(2-(2-hydroxyethoxy)ethoxy)ethoxy) ethyl phosphate as clear oil (50% yield). LCMS (ES+) m/z calcd. for $C_{22}H_{31}O_8P$ [(M+H)+]: 455, found: 455.

To a solution of dibenzyl 2-(2-(2-(2-hydroxyethoxy) ethoxy)ethoxy)ethyl phosphate (500 mg, 1.1 mmol) and pyridine (200 mg, 205 µl, 2.53 mmol) in methylene chloride (6 mL) at −78° C. was added slowly 1-chloroethyl chloroformate (178 mg, 134 µl, 1.24 mmol) in methylene chloride (2 mL). After addition, the reaction mixture was allowed to stir at −78° C. for 1.5 h. Then the cold bath was removed and the reaction mixture was warmed up to room temperature. 1H-NMR showed the completion of the reaction. The reaction mixture was concentrated in vacuo. The residue was reconstituted with diethyl ether. The solids in the ethereal solution were filtered off and washed thoroughly with diethyl ether. The filtrate and washing solutions were combined and concentrated to give carbonic acid 2-(2-{2-[2-(bis-benzyloxy-phosphoryloxy)-ethoxy]-ethoxy}-ethoxy)-ethyl ester 1-chloro-ethyl ester as clear light-yellow thick oil. The crude product was used without further purification.

To a solution of 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (prepared as described in US20100152190A1, 136 mg, 221 µmol) in dry dimethyl formamide (10 mL) was added cesium carbonate (359 mg, 1.1 mmol). It was stirred at room temperature for 10 min. Carbonic acid 2-(2-{2-[2-(bis-benzyloxy-phosphoryloxy)-ethoxy]-ethoxy}-ethoxy)-ethyl ester 1-chloro-ethyl ester, the thick yellow oil got from previous step (617 mg, 1.1 mmol), dissolved in 3 mL of dry dimethyl formamide was added to the above mixture and stirred at room temperature overnight. The reaction was completed as shown by LC-MS. The reaction mixture was poured into water. Then it was extracted with ethyl acetate (2×). The ethyl acetate layers were combined and washed with water and brine. It was dried over anhydrous sodium sulfate, filtered and concentrated to give a crude, which was purified with flash chromatography (30-100% ethyl acetate in hexane over 30 min) to give 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-dibenzyloxyphosphoryloxy-ethoxy)-ethoxy]-ethoxy}-ethoxycarbonyloxy)-ethyl ester as a clear oil (102 mg, 40.5% yield). LCMS (ES+) m/z calcd. for $C_{56}H_{62}Cl_2F_2N_3O_{14}P$ [(M+H)+]: 1140, found: 1140.

EXAMPLE 55

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-phosphonooxy-ethoxy)-ethoxy]-ethoxy}-ethoxycarbonyloxy)-ethyl ester

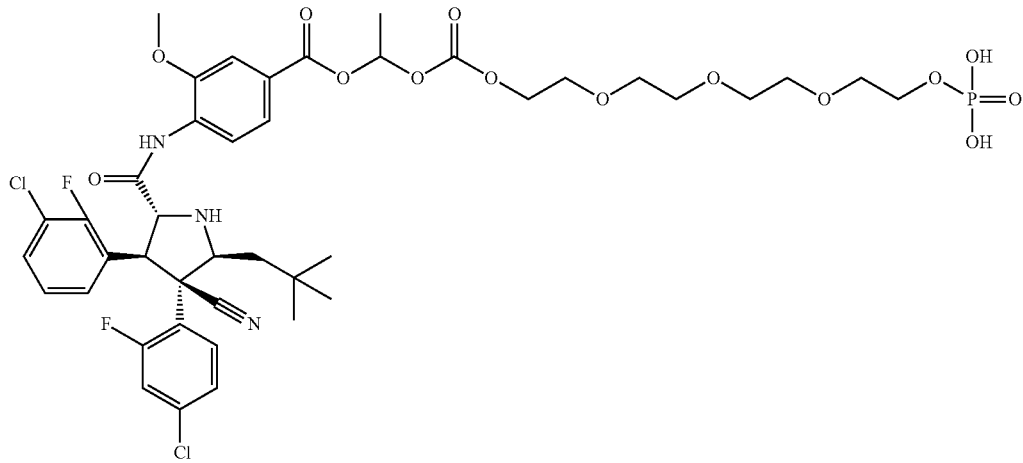

M.W. 960.73 C$_{42}$H$_{50}$Cl$_2$F$_2$N$_3$O$_{14}$P

In a 25 mL three-necked flask, 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-dibenzyloxyphosphoryloxy-ethoxy)-ethoxy]-ethoxy}-ethoxycarbonyloxy)-ethyl ester (100 mg, 87.6 μmol) was combined with isopropyl alcohol (5 mL) at room temperature. Then 10% palladium on carbon (46.6 mg, 43.8 μmol) was added. The flask was flushed with nitrogen, and then replaced with hydrogen. The reaction mixture was stirred at room temperature under hydrogen balloon for 30 min.

The reaction mixture was filtered through a Celite cake to remove the catalyst. The Celite cake was washed thoroughly with isopropyl alcohol. The filtrate and washing solutions were combined and concentrated to give a crude, which was purified with Gilson reverse phase high-performance liquid chromatography (50-80% gradient of acetonitrile in water over 10 min) to give 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-phosphonooxy-ethoxy)-ethoxy]-ethoxy}-ethoxycarbonyloxy)-ethyl ester as white solids (6 mg, 7% yield). LCMS (ES+) m/z calcd. for C$_{42}$H$_{50}$Cl$_2$F$_2$N$_3$O$_{14}$P [(M+H)+]: 960, found: 960.

EXAMPLE 56

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.02% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.02% BSA, shake at room temperature for 30 minutes and read using a TRF-capable plate reader at 665 and 615 nm (Victor 5, Perkin ElmerWallac). If not specified, the reagents were purchased from Sigma Chemical Co.

Activity data for some of the Example compounds expressed as IC$_{50}$:bsa:0.02% are as follows:

| Example Number | IC$_{50}$ (uM, with 0.02% BSA) |
| --- | --- |
| 1 | 0.0296 |
| 2 | 0.0108 |
| 3 | 0.0163 |
| 4 | 0.0187 |
| 5 | 0.0104 |
| 6 | 0.0145 |
| 7 | 0.045 |
| 8 | 0.0536 |
| 9 | 0.116 |
| 10 | 0.0536 |
| 11A | 0.0101 |
| 11B | 0.0194 |
| 12 | 0.0238 |
| 13 | 0.0142 |
| 14 | 0.012 |
| 15 | 0.0128 |
| 16 | 0.0134 |
| 17 | 0.0117 |
| 18 | 0.0131 |

-continued

| Example Number | IC$_{50}$ (uM, with 0.02% BSA) |
|---|---|
| 19 | 0.0514 |
| 20 | 0.00584 |
| 21 | 0.0435 |
| 22 | 0.00713 |
| 23 | 0.011 |
| 24 | 0.00439 |
| 26 | 0.00582 |
| 28 | 0.00819 |
| 30 | 0.0043 |
| 31 | 0.162 |
| 33 | 0.00822 |
| 34 | 0.00909 |
| 35 | 0.00525 |
| 36 | 0.0202 |
| 37 | 0.00714 |
| 38 | 0.00421 |
| 39 | 0.00506 |
| 40 | 0.00444 |
| 41 | 0.00518 |
| 42 | 0.00509 |
| 43 | 0.00569 |
| 44 | 0.00486 |
| 45 | 0.00463 |
| 46 | 0.0408 |
| 47 | 0.0303 |
| 48 | 0.00696 |
| 49 | 0.0801 |
| 50 | 0.0265 |
| 51 | 0.00514 |
| 52 | 0.0267 |
| 53 | 0.0034 |
| 54 | 0.00421 |
| 55 | 0.00475 |

What is claimed is:

1. A compound of the formula (I)

wherein

X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl and lower alkynyl, Z is lower alkoxy, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, $R_2$ is a substituted phenyl selected from:

W is F, Cl or Br,
V is H or F,
$R_3$ is selected from the group consisting of hydrogen, lower alkyl and substituted lower alkyl,
$R_4$ is selected from $R_5$ is selected from the group consisting of lower alkyl, substituted lower alkyl, heterocycle, substituted heterocycle, cycloalkyl, substituted cycloalkyl, natural and unnatural amino acids, —(OCH$_2$CH$_2$)$_n$—OH, —(OCH$_2$CH$_2$)$_n$—OCH$_3$, —(NCH$_2$CH$_2$)$_n$—OH, —(NCH$_2$CH$_2$)$_n$—OCH$_3$ and —(OCH$_2$CH$_2$)$_n$—OP(O)(OR$_6$)$_2$, wherein n is from 3 to 60, $R_6$ is hydrogen or benzyl, or a pharmaceutically acceptable salt or ester thereof.

2. The compound of claim 1 wherein
X is selected from H, F or Cl,
Y is selected from H, F or Cl,
$R_1$ is lower alkyl or substituted lower alkyl,
$R_3$ is hydrogen or lower alkyl,
$R_5$ is selected from the group consisting of lower alkyl, substituted lower alkyl natural and unnatural amino acids, —(OCH$_2$CH$_2$)$_n$—OH, —(OCH$_2$CH$_2$)—OCH$_3$, —(NCH$_2$CH$_2$)$_n$—OH, —(NCH$_2$CH$_2$)$_n$—OCH$_3$, —(OCH$_2$CH$_2$)$_n$—OP(O)(OR$_6$)$_2$, wherein n is from 40-60 and $R_6$ is hydrogen or a pharmaceutically acceptable salt thereof.

3. The compound of claim 1 wherein
X is selected from H, F or Cl,
Y is selected from H, F or Cl,
$R_1$ is lower alkyl or substituted lower alkyl,
$R_3$ is hydrogen or lower alkyl,
$R_5$ is selected from —(OCH$_2$CH$_2$)$_n$—OH or —(OCH$_2$CH$_2$)$_n$—OCH$_3$ wherein n is from 45-55 and
$R_6$ is hydrogen
or a pharmaceutically acceptable salt thereof.

4. The compound of claim 3 wherein
$R_5$ is selected from —(OCH$_2$CH$_2$)$_n$—OH or —(OCH$_2$CH$_2$)$_n$—OCH$_3$ wherein n is about 45-50
or a pharmaceutically acceptable salt thereof.

5. The compound of claim 1 selected from the group consisting of 1-(Ethyl(isopropyl)carbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S ,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid di-tert-butoxy-phosphoryloxymethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[bis-(2-methoxy-ethyl)-carbamoyloxy]-ethyl ester, 4-Methyl-piperazine-1-carboxylic acid 1-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethyl ester, 1-Acetoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, Rac-1-(isobutyryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid acetoxymethyl ester, 1-(Cyclohexyloxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, Rac-1-(isopropoxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethyl morpholine-4-carboxylate and Morpholine-4-carboxylic acid (R)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester.

6. The compound of claim 1 selected from the group consisting of

Morpholine-4-carboxylic acid (S)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester, Rac-1-tert-butyl 4-(1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl)piperazine-1,4-dicarboxylate, Piperazine-1-carboxylic acid 1-(4-{[(2R,3S,4R,5S)-4-(4-chloro-2-fluoro-phenyl)-3-(3-chloro2-fluoro-phenyl)-4-cyano-5-(2,2-dimethyl-propyl)-pyrrolidine-2-carbonyl]-amino}-3-methoxy-benzoyloxy)-ethyl ester di-hydrochloride, Rac-1,1-Dioxo-thiomorpholine-4-carboxylic acid 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,2-dimethyl-[1,3]dioxolan-4-ylmethylcarbamoyloxy)-ethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,3-dihydroxy-propylcarbamoyloxy)-ethyl ester, 1-(Tetrahydro-2H-pyran-4-ylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-{2-[2-(2-methoxy-ethoxy)-ethoxy]-ethoxycarbonyloxy}-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-methoxy-ethoxy)-ethoxy]-ethoxy}-ethoxycarbonyloxy)-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[2-(2-{2-[2-(2-methoxy-ethoxy)-ethoxy]-ethoxy}-ethoxy)-ethoxycarbonyloxy]-ethyl ester and 21-oxo-2,5,8,11,14,17,20,22-octaoxatetracosan-23-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate.

7. The compound of claim 1 selected from the group consisting of

4-{[(2R,3S,4R,5S)-3-(3-Chloro-2-fluoro-phenyl)-4-(4-chloro-2-fluoro -phenyl)-4-cyano-5-(2,2-dimethyl-propyl)-pyrrolidine-2-carbonyl]-amino}-3-methoxy-benzoic acid 1-mPEG-carbonyloxy-ethyl ester, 1-(2-(Benzyloxy)-2-oxoethylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 2-((1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethoxy)carbonylamino)acetic acid, (S)-2-[1-(4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethoxycarbonylamino]-pentanedioic acid, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-((S)-1-carboxy-ethylcarbamoyloxy)-ethyl ester, 2-(((4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)methoxy)-carbonylamino)acetic acid, (S)-Dibenzyl 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)-pentanedioate and (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)pentanedioic acid.

8. The compound of claim 1 selected from the group consisting of 15-methyl-12-oxo-2,5,8,11,13-pentaoxahexadecan-14-yl 4-((2R,3S,4R,5S)-3-(3-chloro-2-fluorophenyl)-4-(4- chloro-2-fluorophenyl)-4-cyano-5-neopentylpyrroli-
dine-2-carboxamido)-3-methoxybenzoate,
3-Oxo-2,4,7,10,13-pentaoxatetradecyl 4-((2R,3S,4R,5S)-
3-(3-chloro-2-fluorophenyl)-4-(4-chloro-2-fluorophe-
nyl)-4-cyano-5-neopentylpyrrolidine-2-carboxamido)-
3-methoxybenzoate,
3-Oxo-2,4,7,10,13,16,19-heptaoxaicosyl 4-((2R,3S,4R,
5S)-3-(3-chloro-2-fluorophenyl)-4-(4-chloro-2-fluo-
rophenyl)-4-cyano-5-neopentylpyrrolidine-2-carboxa-
mido)-3-methoxybenzoate,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-methyl ester,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-ethyl ester,
3-Oxo-2,4,7,10,13-pentaoxatetradecyl 4-((2R,3S,4R,5S)-
3-(3-chloro-2-fluorophenyl)-4-(4-chloro-2-fluorophe-
nyl)-4-cyano-5-neopentylpyrrolidine-2-carboxamido)-
3-methoxybenzoate,
27-Oxo-2,5,8,11,14,17,20,23,26,28-decaoxatriacontan-
29-yl 4-((2R,3S,4R,5S)-3-(3-chloro-2-fluorophenyl)-4-
(4-chloro-2-fluorophenyl)-4-cyano-5-neopentylpyrro-
lidine-2-carboxamido)-3-methoxybenzoate,
24-Oxo -2,5,8,11,14,17,20,23,25-nonaoxaheptacosan-26-
yl 4-((2R,3S,4R,5S)-3-(3-chloro-2-fluorophenyl)-4-(4-
chloro-2-fluorophenyl)-4-cyano-5-neopentylpyrroli-
dine-2-carboxamido)-3-methoxybenzoate, and
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-ethyl amide.

9. The compound of claim 1 selected from the group consisting of
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-ethyl amide,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-methyl amide,
(S)-2-(((4-((2R,3S,4R,5S)-3-(3-chloro-2-fluorophenyl)-
4-(4-chloro-2-fluorophenyl)-4-cyano-5-neopentylpyr-
rolidine-2-carboxamido)-3-methoxybenzoyloxy)meth-
oxy)carbonylamino)propanoic acid,
Dibenzyl 4-{[(2R,3S,4R,5S)-4-(4-Chloro-2-fluoro-phe-
nyl)-3-(3-chloro-2-fluoro-phenyl)-4-cyano-5-(2,2-dim-
ethyl-propyl)-pyrrolidine-2-carbonyl]-amino}-3-meth-
oxy-benzoic acid 2-{2-[2-(2-phosphonooxy-ethoxy)-
ethoxy]-ethoxy}-ethoxycarbonyloxymethyl ester,
4-{[(2R,3S,4R,5S)-4-(4-Chloro-2-fluoro-phenyl)-3-(3-
chloro-2-fluoro-phenyl)-4-cyano-5-(2,2-dimethyl-pro-
pyl)-pyrrolidine-2-carbonyl]-amino}-3-methoxy-ben-
zoic acid 2-{2-[2-(2-phosphonooxy-ethoxy)-ethoxy]-
ethoxy}-ethoxycarbonyloxymethyl ester,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid phosphonooxymethyl ester; compound with
trifluoro-acetic acid,
1-(((3aR,5R,6S,6aR)-5-((R)-2,2-dimethyl-1,3-dioxolan-
4-yl)-2,2-dimethyltetrahydrofuro[3,2-d][1,3]dioxol-6-
yloxy)carbonyloxy)ethyl 4-((2R,3S,4R,5S)-3-(3-
chloro-2-fluorophenyl)-4-(4-chloro-2-fluorophenyl)-4-
cyano-5-neopentylpyrrolidine-2-carboxamido)-3-
methoxybenzoate,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-[(2R,3R,4R,5S)-2-((R)-1,2-dihydroxy-
ethyl)-4,5-dihydroxy-tetrahydro-furan-3-
yloxycarbonyloxy]-ethyl ester,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-(2-{2-[2-(2-dibenzyloxyphosphoryloxy-
ethoxy)-ethoxy]-ethoxy}-ethoxycarbonyloxy)-ethyl
ester and
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-(2-{2-[2-(2-phosphonooxy-ethoxy)-
ethoxy]-ethoxy}-ethoxycarbonyloxy)-ethyl ester.

10. The compound of claim 1 selected from the group consisting of
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-[2-(2-{2-[2-(2-methoxy-ethoxy)-ethoxy]-
ethoxy}-ethoxy)-ethoxycarbonyloxy]-ethyl ester,
4-{[(2R,3S,4R,5S)-3-(3-Chloro-2-fluoro-phenyl)-4-(4-
chloro -2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-ethyl ester,
15-methyl-12-oxo-2,5,8,11,13-pentaoxahexadecan-14-yl
4-((2R,3S,4R,5S)-3-(3-chloro-2-fluorophenyl)-4-(4-
chloro-2-fluorophenyl)-4-cyano-5-neopentylpyrroli-
dine-2-carboxamido)-3-methoxybenzoate,
3-Oxo-2,4,7,10,13-pentaoxatetradecyl 4-((2R,3S,4R,5S)-
3-(3-chloro-2-fluorophenyl)-4-(4-chloro-2-fluorophe-
nyl)-4-cyano-5-neopentylpyrrolidine-2-carboxamido)-
3-methoxybenzoate,
3-Oxo-2,4,7,10,13,16,19-heptaoxaicosyl 4-((2R,3S,4R,
5S)-3-(3-chloro-2-fluorophenyl)-4-(4-chloro-2-fluo-
rophenyl)-4-cyano-5-neopentylpyrrolidine-2-carboxa-
mido)-3-methoxybenzoate,
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-ethyl ester,
3-Oxo-2,4,7,10,13-pentaoxatetradecyl 4-((2R,3S,4R,5S)-
3-(3-chloro-2-fluorophenyl)-4-(4-chloro-2-fluorophe-
nyl)-4-cyano-5-neopentylpyrrolidine-2-carboxamido)-
3-methoxybenzoate,
27-Oxo-2,5,8,11,14,17,20,23,26,28-decaoxatriacontan-
29-yl 4-((2R,3S,4R,5S)-3-(3-chloro-2-fluorophenyl)-4-
(4-chloro-2-fluorophenyl)-4-cyano-5-neopentylpyrro-
lidine-2-carboxamido)-3-methoxybenzoate,
24-Oxo-2,5,8,11,14,17,20,23,25-nonaoxaheptacosan-26-
yl 4-((2R,3S,4R,5S)-3-(3-chloro-2-fluorophenyl)-4-(4-
chloro-2-fluorophenyl)-4-cyano-5-neopentylpyrroli-
dine-2-carboxamido)-3-methoxybenzoate and
4-{[(2R,3S,4R,5S)-3-(3-Chloro-2-fluoro-phenyl)-4-(4-
chloro-2-fluoro-phenyl)-4-cyano-5-(2,2-dimethyl-pro-
pyl)-pyrrolidine-2-carbonyl]-amino}-3-methoxy-ben-
zoic acid 1-mPEG-carbonyloxy-ethyl amide.

11. The compound: 4-{[(2R,3S,4R,5S)-3-(3-Chloro-2-fluoro-phenyl)-4-(4-chloro-2-fluoro-phenyl)-4-cyano-5-(2, 2-dimethyl-propyl)-pyrrolidine-2-carbonyl]-amino}-3-methoxy-benzoic acid 1-mPEG-carbonyloxy-ethyl ester.

12. A pharmaceutical composition comprising a compound according to claim 1 and a therapeutically inert carrier.

13. An injectable pharmaceutical formulation comprising a compound according to claim 1 and a pharmaceutically acceptable diluent.

14. An injectable pharmaceutical formulation comprising the compound of claim 12 and a pharmaceutically acceptable diluent.

15. The compound according to claim 7, wherein the mPEG moiety of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester has an average molecular weight of approximately 750.

16. The compound according to claim 8, wherein the mPEG moiety of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester has an average molecular weight of approximately 750.

17. The compound according to claim 8, wherein the mPEG moiety of 4-{[(2R,3S ,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester has an average molecular weight of approximately 2000.

18. The compound according to claim 8, wherein the mPEG moiety of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester has an average molecular weight of approximately 2200.

19. The compound according to claim 8, wherein the mPEG moiety of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester has an average molecular weight of approximately 2000.

20. The compound according to claim 8, wherein the mPEG-NH$_2$ moiety of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide has an average molecular weight of approximately 550.

21. The compound according to claim 8, wherein the mPEG moiety of 4-{[(2R,3S ,4R, 5S)-3-(3-Chloro-2-fluoro-phenyl)-4-(4-chloro -2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide has an average molecular weight of approximately 1000.

22. The compound according to claim 9, wherein the mPEG-NH$_2$ moiety of 4-{[(2R,3S ,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide has an average molecular weight of approximately 2000.

23. The compound according to claim 9, wherein the mPEG-NH$_2$ moiety of 4-{[(2R,3S ,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide has an average molecular weight of approximately 2000.

24. The compound according to claim 9, wherein the mPEG-NH$_2$ moiety of 4-{[(2R,3S,4R, 5S)-3-(3-Chloro -2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide has an average molecular weight of approximately 1000.

25. The compound according to claim 9, wherein the mPEG-NH$_2$ moiety of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide has an average molecular weight of approximately 550.

26. The compound according to claim 11, having an average molecular weight of approximately 2700.

27. The compound according to claim 11, having an average molecular weight of approximately 2900.

* * * * *